US005627266A

United States Patent [19]
Wainwright et al.

[11] Patent Number: 5,627,266
[45] Date of Patent: May 6, 1997

[54] ENDOTOXIN BINDING AND NEUTRALIZING PROTEIN AND USES THEREOF

[75] Inventors: Norman R. Wainwright, Falmouth; Thomas J. Novitsky, E. Falmouth, both of Mass.

[73] Assignee: Associates of Cape Cod, Inc., Falmouth, Mass.

[21] Appl. No.: 476,940

[22] Filed: Jun. 7, 1995

Related U.S. Application Data

[62] Division of Ser. No. 264,244, Jun. 22, 1994, which is a continuation of Ser. No. 883,457, May 15, 1992, abandoned, which is a continuation-in-part of Ser. No. 701,501, May 16, 1991, abandoned, which is a continuation-in-part of Ser. No. 480,957, Feb. 16, 1990, abandoned, which is a division of Ser. No. 210,575, Jun. 23, 1988, abandoned.

[51] Int. Cl.$^6$ .................................................. C07K 14/00
[52] U.S. Cl. ............................................................. 530/350
[58] Field of Search ............................................. 530/350

[56] References Cited

U.S. PATENT DOCUMENTS

| | | | |
|---|---|---|---|
| 3,944,391 | 3/1976 | Harris et al. | 23/230 |
| 4,107,077 | 8/1978 | Sullivan, Jr. et al. | 252/408 |
| 4,188,264 | 2/1980 | Iwanaga et al. | 23/230 |
| 4,273,557 | 6/1981 | Juranas | 23/230 |
| 4,357,142 | 11/1982 | Schall, Jr. et al. | 23/230 |
| 4,652,639 | 3/1987 | Stabinsky | 536/23.5 |
| 4,713,347 | 12/1987 | Mitchell et al. | 436/501 |
| 4,758,655 | 7/1988 | Houghten | 530/324 |
| 4,780,529 | 10/1988 | Hao | 530/350 |
| 4,906,567 | 3/1990 | Connelly | 435/7 |
| 4,918,163 | 4/1990 | Young et al. | 530/387 |
| 4,977,085 | 12/1990 | Sprague et al. | 435/212 |
| 5,001,048 | 3/1991 | Taylor et al. | 435/4 |
| 5,057,598 | 10/1991 | Pollack et al. | 530/387 |
| 5,068,314 | 11/1991 | Nakamura et al. | 530/317 |
| 5,089,274 | 2/1992 | Marra et al. | 424/534 |
| 5,171,739 | 12/1992 | Scott | 514/12 |
| 5,179,006 | 1/1993 | Matuura et al. | 435/23 |
| 5,316,911 | 5/1994 | Baek et al. | 435/7.9 |

FOREIGN PATENT DOCUMENTS

| | | |
|---|---|---|
| 0056210 | 7/1982 | European Pat. Off. . |
| 0206783 | 12/1986 | European Pat. Off. . |
| 0224830 | 6/1987 | European Pat. Off. . |
| 0279517 | 8/1988 | European Pat. Off. . |
| 59-027828 | 2/1984 | Japan . |
| 59-28474 | 2/1984 | Japan . |
| 57-135681 | 5/1984 | Japan . |
| 2019563 | 10/1979 | United Kingdom . |
| WO83/02123 | 6/1983 | WIPO . |
| WO89/12644 | 12/1989 | WIPO . |

OTHER PUBLICATIONS

Weary et al., "A Manufacturer's Guide to Depyrogenation", *BioPharm*, pp. 22–29 (Apr., 1988).
Williams et al., "Limulus Anti-LPS Factor Reduces Lethality of Endotoxin in vivo and Blocks Effects on Vascular Contractility in vitro", *Abstracts of the First Congress of the International Endotoxin Society*, Abstract No. III-P-64, p. 82 (1990).
International Search Report for the corresponding PCT Application, No. PCT/US92/03983.
Obayashi, T., et al., "Endotoxin-Inactivating Activity in Normal and Pathological Human Blood Samples," *Infect. Immun.* 53(2):294–297 (Aug. 1986).
English abstracts for Japanese Patent Document No. J59027828 (Doc. Ref. AM2), Derwent Accession Nos. 84–072449/12 and 84–05155.
Aketagawa et al., "Primary Structure of Limulus Anticoagulant Anti-Lipopolysaccharide Factor", *J. Biol. Chem.* 261(6):7357–7365 (Jun. 5, 1986).
Aldrich Chemical Company, Inc., Catalogue entitled *Aldrich Fine Chemicals*, p. 1115 (1986).
Alpert et al., "Endotoxin Binding Protein (EBP) Protects Rabbits from Meningococcal Endotoxic Shock", *Pediatric Res.* 27(4): Abstract #973 (1990).
Alpert, G. et al., "Limulus Antilipopolysaccharide Factor Protects Rabbits from Meningococcal Endotoxin Shock", *J. Infect. Dis.* 165:494–500 (1992).
Brade et al., "Characterization of Murine Monoclonal and Murine, Rabbit, and Human Polyclonal Antibodies Against Chlamydial Lipopolysaccharide", *Infect. Immun.* 58(1):205–213 (Jan., 1990).
Case et al., "Detection of Endotoxin in Antibiotic Solutions with Limulus Amoebocyte Lysate", *Antimicrobial Agents and Chemotherapy* 23(5):649–652 (May, 1983).
Chan et al., "Pentoses and Lignin", in: *Advances in Biochemical Engineering/Biotechnology*, A. Fiechter (Ed.), New York: Springer-Verlag, pp. 120–126 (1983).
Chia et al., "Lipopolysaccharide (LPS)–Reactive Monoclonal Antibodies Fail to Inhibit LPS-Induced Tumor Necrosis Factor Secretion by Mouse-Derived Macrophages", *J. Infect. Dis.* 159(5):872–880 (May, 1989).
Danner et al., "Purification, Toxicity, and Antiendotoxin Activity of Polymyxin B Nonapeptide", *Antimicrobial Agents and Chemotherapy* 33(9), 1428–1434 (Sep., 1989).
Dawson et al., "Microbes, Endotoxins and Water", *Pharm. Eng.* 8(2):9–12 (Mar./Apr., 1988).

(List continued on next page.)

*Primary Examiner*—Robert A. Wax
*Assistant Examiner*—K. Cochrane Carlson
*Attorney, Agent, or Firm*—Sterne, Kessler, Goldstein & Fox P.L.L.C.

[57] ABSTRACT

Endotoxin binding/neutralizing proteins capable of binding endotoxin in vivo, thereby neutralizing the toxic effect or bioactivity of endotoxin which are isolated from a horseshoe crab such as *Limulus polyphemus*, pharmaceutical compositions and pharmaceutical uses of the proteins, a method of purifying the proteins and an assay for endotoxin based on the proteins, are disclosed.

3 Claims, 16 Drawing Sheets

OTHER PUBLICATIONS

Dayhoff et al., "A Model of Evolutionary Change in Proteins", *Atlas of Protein Sequence and Structure* 5:88–99 (1972).

Desch, C.E. et al., "Antilipopolysaccharide Factor from Horseshoe Crab, *Tachypleus tridentatus*, Inhibits Lipopolysaccharide Activation of Cultured Human Endothelial Cells", *Infect. Immun.*, 57:1612–1614 (May, 1989).

Dunn et al., "Protective Capacity of Polyclonal and Monoclonal Antibodies Directed Against Endotoxin During Experimental Sepsis", *Arch. Surg.* 123:1389–1393 (Nov., 1988).

Flaschel, "Ultrafiltration for the Separation of Biocatalysts", in: *Advances in Biochemical Engineering/Biotechnology*, A. Fiechter (Ed.), New York: Springer–Verlag, pp. 120, 123 (1983).

Garcia, C.T. et al., "Effect of Endotoxin Neutralizing Protein (ENP) on Gram Negative Sepsis in a Rabbit Model", *Ped. Res.* 29:117A, Abstract No. 1012 (Apr., 1991).

Gould, "Endotoxin in Vertebrate Cell Culture: Its Measurement and Significance", *In Vitro Monograph* 5, Tissue Culture Association, Rockville, MD, pp. 125–136 (1984).

Iwanaga, S. et al., "Primary Structure of Anti–Lipopolysaccharide Factor from American Horseshoe Crab, *Limulus polyphemus*", International Symposium on Pyrogen, Z. Haijun (Ed.), Xiamen (Amoy), China, pp. 84–87 (Jun., 1987).

Kawasaki et al., "Analysis of Endotoxin Fever in Rabbits by Using a Monoclonal Antibody to Tumor Necrosis Factor (Cachectin)", *Infec. Immun.* 57(10):3131–3135 (Oct., 1989).

Kupperman, N. et al., "Recombinant Endotoxin Neutralizing Protein from *L. polyphemus* Reduces Mortality from *E. coli* Sepsis in Rat Model", *Pediatric Res.* 31(4):Abstract No. 176 (May, 1992).

Liang et al., "Studies on Limulus Amoebocyte Lysate", *J. Biol. Chem.* 255(12):5586–5590 (Jun. 25, 1980).

Liang et al., "Studies on Limulus Amoebocyte", *J. Biol. Chem.* 256(10):4968–4972 (May 25, 1981).

McCartney, "The Limulus Amoebocyte Lysate Assay for Bacterial Endotoxins", *Chem. Abstr.* 105:185, Abstract No. 73795j (1986).

McKenna, T.M., "Recovery of Vascular Tissue Contractile Function During Sustained Endotoxin Exposure", *Am. J. Physiol.* 263:H1628–H1631 (1992).

Minetti et al., "Purification and Characterization of an Endotoxin–Binding Protein with Protease Inhibitory Activity from Limulus Amoebocytes", *J. Biol. Chem.* 266(31):20773–20780 (Nov. 5, 1991).

Morita et al., "Isolation and Biological Activities of Limulus Anticoagulant (Anti–LPS Factor) Which Interacts with Lipopolysacharide (LPS)", *J. Biochem.* 97(6):1611–1620 (1985).

Muta et al., "Primary Structure of Anti–Lipopolysaccharide Factor from American Horseshoe Crab, *Limulus polyphemus*", *J. Biochem.* 101(6):1321–1330 (Jun., 1987).

Nachum et al., "Inactivation of Endotoxin by Limulus Amoebocyte Lysate", *J. Invert. Pathol.* 32:51–58 (1978).

Nakamura et al., "Endotoxin–Mediated Limulus Proclotting Enzyme Activator and Detection of a Previously Undescribed Protease (Protease N)", *Biochem. Biophys. Res. Commun.* 108(4):1619–1623 (1982).

Novitsky et al., "Instrumentation—A New Approach for Monitoring Bacteria: The Kinetic LAL Assay", in: *Ultrapure Water*, Associates of Cape Cod, Inc. (Nov./Dec., 1985).

Novitsky, "Monitoring and Validation of High Purity Water Systems with the Limulus Amoebocyte Lysate Test for Pyrogens", *Pharm. Eng.* (reprinted) (Mar./Apr., 1984).

Novitsky et al., "Quantification of Endotoxin Inhibition in Serum and Plasma Using a Turbidimetric LAL Assay", in: *Bacterial Endotoxins: Structure, Biomedical Significance, and Detection with the Limulus Amoebocyte Lysate Test*, New York: Alan R. Liss, Inc., pp. 181–193 (1985).

Novitsky et al., "Turbidimetric Method for Quantifying Serum Inhibition of Limulus Amoebocyte Lysate", *J. Clin. Microbiol.* 20(2):211–216 (Feb., 1985).

Obayashi et al., "Endotoxin–Inactivating Activity in Normal and Pathological Human Blood Samples", *Chem. Abstr.* 105:95431q (1986).

Ooi et al., "Endotoxin–Neutralizing Properties of the 25kD N–Terminal Fragment and a Newly Isolated 30 kD C–Terminal Fragment of the 55–60 kD Bactericidal/Permeability–Increasing Protein of Human Neutrophils", *J. Exp. Med.* 174:649–655 (Sep., 1991).

Ramadori et al., "Biosynthesis of Lipopolysaccharide–Binding Protein in Rabbit Hepatocytes", *Pathobiology* 58:89–94 (1990).

Saladino, R. et al., "Effect of an Endotoxin Neutralizing Protein in an *E. coli* Sepsis Model in the Rabbit", *Pediatric Res.* 31(4):Abstract #195 (1992).

Salles et al., "Protective Effects of Murine Monoclonal Antibodies in Experimental Septicemia: *E. coli* Antibodies Protect Against Different Serotypes of *E. coli*", *J. Infect. Dis.* 159(4):641–647 (Apr., 1989).

Scheifele et al., "Evaluation of the Limulus Test for Endotoxemia in Neonates with Suspected Sepsis", *J. Pediatrics* 98(6):899–903 (Jun., 1981).

Siber, G.R. et al., "Effect of a Recombinant Endotoxin Neutralizing Protein from *Limulus polyphemus* on Gram–negative Sepsis", in: *Bacterial Endotoxin: Recognition and Effector Mechanisms*, Levin, J. et al. (Eds.), Amsterdam: Elsevier Science Publishers B.V., pp. 379–386 (1993).

Sigma® Chemical Company, catalogue entitled *Biochemicals, Organic Compounds and Diagnostic Reagents for Research*, St. Louis, MO, p. 1539 (1991).

Sofer et al., "Designing an Optimal Chromatographic Purification Scheme for Proteins", *BioTechniques* 1(4):198–203 (1983).

Sullivan et al., "Comparison of the Limulus Amoebocyte Lysate Test with Plate Counts and Chemical Analyses for Assessment of the Quality of Lean Fish", *Appl. Env. Microbiol.* 45(2):720–722 (Feb., 1983).

Tallon, M.A. et al., "Synthesis and Biological Activity of Amino Terminus Extended Analogues of the α Mating Factor of *Saccharomyces cerevisiae*", *Biochemistry* 26(24):7767–7774 (Dec. 1, 1987).

Tanaka et al., "Limulus Anti–LPS Factor: An Anticoagulant Which Inhibits the Endotoxin–Mediated Activation of Limulus Coagulation System", *Biochem. Biophys. Res. Commun.* 105(2):717–723 (1982).

Tune et al., "Effects of Anti–Lipid A Human Monoclonal Antibody on Lipopolysaccharide–Induced Toxicity to the Kidney", *J. Urol.* 141:1463–1466 (Jun., 1989).

Wainwright et al., "Endotoxin Binding and Neutralizing Activity by a Protein from *Limulus polyphemus*", in: *Cellular and Molecular Aspects of Endotoxin Reactions*, Nowotny, A. et al. (Eds.), Amsterdam: Elsevier Science Publishers, B.V., pp. 315–325 (1990).

Wainwright et al., "Endotoxin Binding and Neutralizing Activity by a Protein from *Limulus polyphemus*", *Int. Congr. Ser. Excerpta Med.* 923:315–325 (1990).

Wainwright, N.R., "Endotoxin Binding Protein for Treatment of Septic Shock", *Gov. Rep. Announc. Index* 91(16):Abstract No. 143,791 (1991).

Warren et al., "Endotoxin Neutralizing Capacity of Sera from Different Patient Populations Assessed by the Limulus Lysate Test", in: *Detection of Bacterial Endotoxins with the Limulus Amoebocyte Lysate Test*, New York: Alan R. Liss, Inc., pp. 341–348 (Sep. 10, 1987).

Warren, H.S., "Binding and Neutralization of Endotoxin by Limulus Antilipopolysaccharide Factor", *Infect. Immun.* 60(6):2506–2513 (Jun., 1992).

```
  1               5                  10
Asp Gly Ile Trp Thr Gln Leu Ile Phe Leu Val Asn 15                    20              25                    30
His Tyr Arg Ala Leu Ala Thr Leu Trp Ile Gln Ser Gly Asp Phe Gln Phe Leu Asp His Glu Cys 35                    40                    45
Lys Ile Pro Thr Phe Arg Arg Leu Lys Tyr Lys Gly Lys 50              55                    60                    65
Phe Trp Cys Pro Ser Trp Thr Ser Ile Thr Arg Gly Ala Thr Lys Ser Ser Arg 70              75                    80                    85
Ser Gly Ala Val Glu His Ser Val Arg Asn Phe Val Gly Gln Ala Gly Ser Ser 90                    95                    100
Gln Gln Arg Gln Ala Glu Gln Phe Ile Ser Gln Try Asn
```

FIG. 15

```
GAA GCT GAA GCT GAC GGT ATC TGG ACC CAA TTG ATT TTC ACT TTG GTT AAC
Glu Ala Glu Ala Asp Gly Ile Trp Thr Gln Leu Ile Phe Thr Leu Val Asn
                    1                 5                   10
ATT TTG GCC ACC TTA TGG CAG TCC GGT GAT TTT CAA TTC TTG GAC CAC GAA TGT
Ile Leu Ala Thr Leu Trp Gln Ser Gly Asp Phe Gln Phe Leu Asp His Glu Cys
        15                   20                  25                  30
CAC TAC AGA ATC AAG CCA ACT TTC AGA AGA TTG AAG TGG AAA TAT AAG GGT AAA
His Tyr Arg Ile Lys Pro Thr Phe Arg Arg Leu Lys Trp Lys Tyr Lys Gly Lys
                35                  40                  45
TTT TGG TGT CCA TCT TGG ACC TCT ATT ACT GGT AGA GCT ACC AAG TCT TCT AGA
Phe Trp Cys Pro Ser Trp Thr Ser Ile Thr Gly Arg Ala Thr Lys Ser Ser Arg
    50                  55                  60                  65
TCC GGT GCT GTC GAA CAC TCT GTT AGA AAC TTC GTC CCA GCT AAG TCT TCC
Ser Gly Ala Val Glu His Ser Val Arg Asn Phe Val Gly Pro Ala Lys Ser Ser
        70                  75                  80                  85
GGT TTG ATC ACT GAA AGA CAA CAA GCT GAA CAA TTC ATT TCT CAA TAC AAC TGA TAA
Gly Leu Ile Thr Glu Arg Gln Gln Ala Glu Gln Phe Ile Ser Gln Tyr Asn
                90                  95                  100

GCT TGA ATT C
```

FIG. 16

ENDOTOXIN BINDING AND NEUTRALIZING PROTEIN AND USES THEREOF

This application is a division of application Ser. No. 08/264,244, filed Jun. 22, 1994, which is a continuation of application Ser. No. 07/883,457, filed May 15, 1992, abandoned, which is a continuation-in-part of application Ser. No. 07/701,501, filed May 16, 1991, now abandoned, which is a continuation-in-part of application Ser. No. 07/480,957, filed Feb. 16, 1990, now abandoned, which is a divisional of application Ser. No. 07/210,575, filed Jun. 23, 1988 now abandoned.

BACKGROUND OF THE INVENTION

1. Field of the Invention

The present invention is directed to pharmaceutical compositions and uses of an endotoxin binding/neutralizing protein which may be isolated from a horseshoe crab. The invention covers, inter alia, pharmaceutical compositions and pharmaceutical uses of the protein, a method of purifying the protein, and an assay for endotoxin based on this protein.

2. Discussion of the Background

Despite aggressive management, septic shock arising from gram-negative sepsis continues to be a leading cause of death in both surgical and medical patients. Death in such patients usually results from cardiovascular collapse and/or multiple organ system failure. One of the main components of gram-negative bacteria thought to play an integral role in causing septic shock is an outer wall constituent, endotoxin.

Endotoxins are high molecular weight complexes, associated with the outer membrane of gram-negative bacteria, that produce pyrogenic reactions upon intravenous administration. Endotoxin is shed from living bacteria and is also released into the environment when bacteria die and decompose. Since gram-negative bacteria are found in great numbers in air, water, and soil, bacterial endotoxin commonly contaminates raw materials and processing equipment used in the manufacturing of, for example, pharmaceuticals.

Bacterial endotoxin is a complex consisting of lipid, carbohydrate and protein. It is characterized by an overall negative charge, heat stability and high molecular weight. Highly purified endotoxin does not contain protein, and is a lipopolysaccharide (LPS). Depyrogenation can generally be achieved by inactivating or removing endotoxin, depending upon the physicochemical nature of the LPS. LPS consists of three distinct chemical regions, lipid A, which is the innermost region, an intermediate core polysaccharide, and an outermost 0-specific polysaccharide side chain which is responsible for an endotoxin's particular immunospecificity.

Bacterial endotoxins are known to have profound biological effects in animals and humans, and to cause severe medical problems when present. Symptoms include induction of high fever, activation of complement, and hypotenston. It is critical to avoid endotoxin contamination in any pharmaceutical product or medical device which comes into contact with body fluids. High endotoxin levels in sera due to bacterial diseases, such as septicemia, are not easily treated. Antibiotic treatment of the infection only kills the bacteria, leaving the endotoxin from their cell walls free to cause fever.

The horseshoe crab Limulus polyphemus is particularly sensitive to endotoxin. The cells from their hemolymph (amebocytes) undergo a complex series of biochemical reactions resulting in clot formation, analogous to mammalian blood coagulation. This phenomenon has been exploited in the form of bioassays sensitive to very low endotoxin levels. Currently, a bioassay of this type is the method of choice for monitoring pharmaceutical manufacturing and is termed Limulus Amebocyte Lysate (LAL). See U.S. Pat. Nos. 4,276,050, 4,273,557, 4,221,866, 4,201,865, 4,038, 147, 3,944,391 and 3,915,805, each of which is incorporated herein by reference.

It has long been observed that once endotoxin interacts with LAL the toxin is not recoverable from the clot. See Nachum et al, Journal of Invertebrate Pathology, 32:51–58 (1978). This observation led investigators to postulate two alternative explanations. Either the endotoxin is enzymatically degraded during clot formation or it is bound by some factor causing it to lose toxicity. The present inventors initiated experiments to extract the endotoxin inactivating factor from the LAL.

Other research groups have experimented with endotoxin binding proteins, also referred to as anti-LPS factor. To the inventor's knowledge, the following publications resulting from work in this area are the most relevant to this invention:

Tanaka et al, Biochem. Biophys. Res. Comm. 105, 717–723 (1982),

Iwanaga et al, International symposium on Pyrogen, 84–84 (Jun. 23–26, 1987),

Aketagawa et al, J. Biol. Chem. 261, 7354–7365 (1986),

Hao, U.S. Pat. No. 4,677,194 (Jun. 30, 1987), and

Nachum et al, J. Inv. Path. 32, 51–58 (11978).

Tanaka et al, Iwanaga et al, and Aketagawa et al each conducted research on an anti-LPS factor or endotoxin binding protein isolated from a horseshoe crab system. Based on experimental work done in the inventors' laboratory, it appears that a protein involved in the present invention is the same as that isolated by Iwanaga et al and Tanaka et al. However, these publications do not say anything about pharmaceutical utility of the endotoxin binding/neutralizing protein, and it is difficult to predict in vivo activity based on in vitro experimentation. In fact, neither of these references suggests a practical utility for the anti-LPS factor, and in view of the unpredictable nature of in vivo activity, it has previously not been appreciated that the endotoxin binding/neutralizing protein could be used in a pharmaceutical composition. Furthermore, none of the references disclose the use of the endotoxin binding/neutralizing protein for an endotoxin assay, as disclosed in the present invention. It is notable that the present inventors have also discovered certain endotoxin binding/neutralizing protein variants which have amino acid structures that are different from the anti-LPS factor disclosed in the above-described publications.

SUMMARY OF THE INVENTION

Accordingly, it is an object of the present invention to provide pharmaceutical compositions containing therein an endotoxin-binding/neutralizing protein isolated from a horseshoe crab, which compositions are capable of binding and neutralizing endotoxin in vivo.

It is yet another object of this invention to provide pharmaceutical compositions capable of binding and neutralizing endotoxin in vivo and containing therein an endotoxin binding/neutralizing protein corresponding at least to part of the endotoxin binding and neutralizing domain of the endotoxin binding/neutralizing protein isolated from a horseshoe crab in accordance with the invention.

It is yet another object of the present invention to provide a method for reducing endotoxin concentration and/or neutralizing endoxin activity in vivo.

It is yet another object of the present invention to provide a method for purifying an endotoxin binding/neutralizing protein from a horseshoe crab.

It is yet another object of the present invention to provide a method of assaying for endotoxin in a fluid.

These and other objects of the present invention which will hereinafter become more readily apparent, have been provided by purifying an endotoxin binding/neutralizing protein from the horseshoe crab *Limulus polyphemus*, and discovering that it has the capability of binding to and neutralizing endotoxin in vivo. It has also been recognized that this purified endotoxin binding/neutralizing protein is useful in an assay for endotoxin. The present inventors have also discovered that there are certain structural variants of the *Limulus polyphemus* endotoxin binding/neutralizing protein, and it is expected that these materials will also possess endotoxin binding/neutralizing ability such that they may be used in the other aspects of the present invention as well.

The present inventors have also discovered a domain within the endotoxin binding protein which is necessary for endotoxin binding/neutralizing. The present invention thus uses a protein corresponding at least to this endotoxin binding/neutralizing domain and up to the complete protein sequence.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 15 provides the amino acid sequence of the endotoxin binding/neutralizing protein isolated from *Limulus polyphemus* in accordance with the present invention (SEQ. ID. NO. I).

FIG. 16 sets forth a DNA sequence (SEQ. ID. NO. II) encoding a protein corresponding to the endotoxin binding/neutralizing protein of the present invention having attached to its amino terminus the tetrapeptide Glu-Ala-Glu-Ala. The so modified endotoxin binding/neutralizing protein is SEQ. ID. NO. III. This DNA sequence is equipped with yeast preferred codons and possesses unique restriction enzyme recognition sites for convenient modification of the sequence.

DESCRIPTION OF THE PREFERRED EMBODIMENTS

Figure 1:
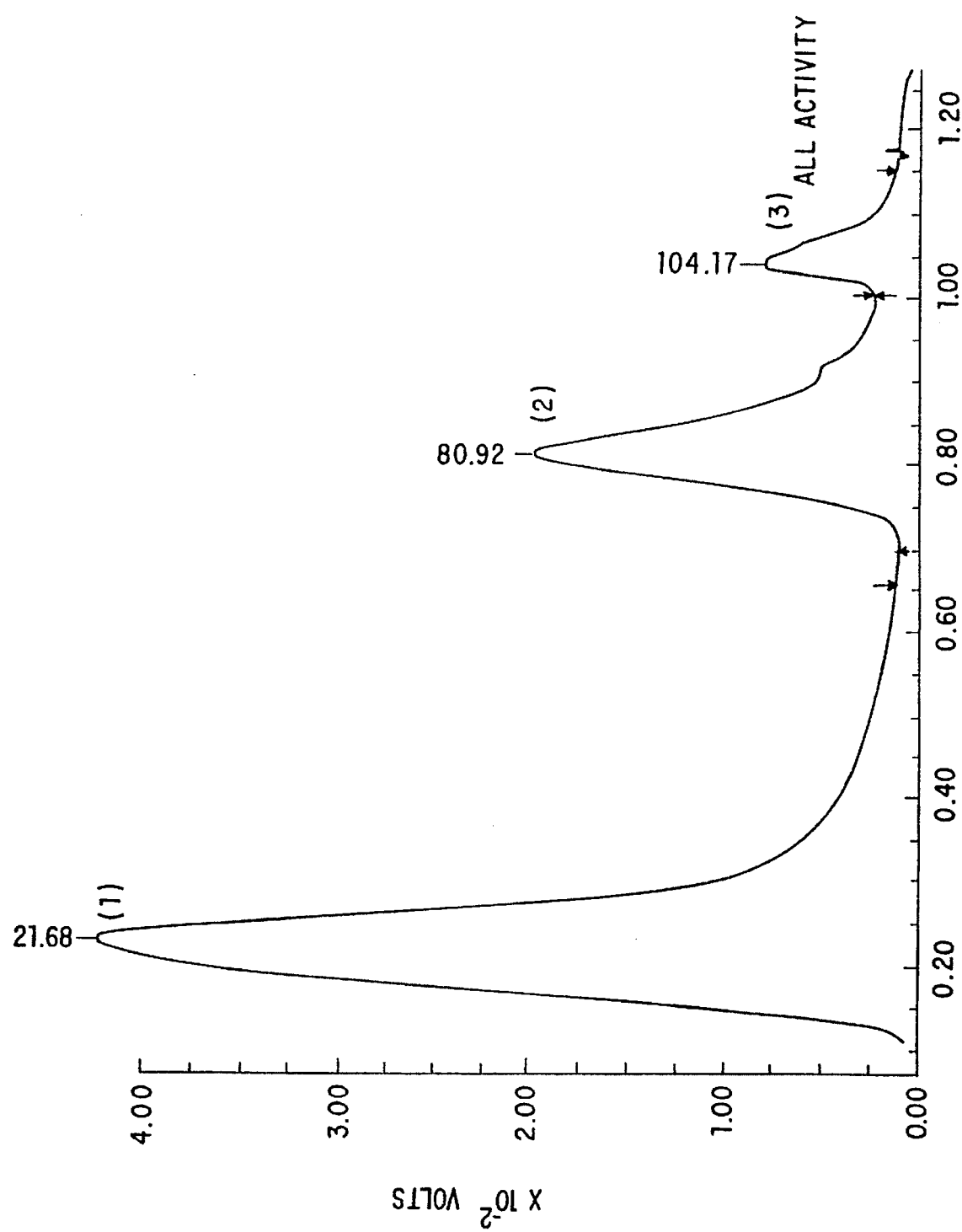
FIG. 1 shows cation exchange chromatographic purification of Limulus endotoxin binding protein using CM-Sepharose resin. Peak 1: flow through, Peak 2: 0.25M NaCl elution, Peak 3: 1M NaCl elution.

The endotoxin binding/neutralizing protein of the present invention may be isolated from any horseshoe crab. For example, any of the four known species of horseshoe crabs could be used. These species are:

*Limulus polyphemus*

*Tachypleus gigas*

*Tachypleus tridentatus*

*Carcinoscorpius rotundicauda*

Especially preferred among these is *Limulus polyphemus*, the horseshoe crab which is found along the North American coast. The endotoxin binding/neutralizing protein may be isolated by a procedure which is summarized hereinbelow. The procedure is illustrated for the Limulus horseshoe crab, but these procedures may be applied to any known horseshoe crab, as recited herein.

It was surprisingly found that the cellular debris produced during lysate production from Limulus amebocytes contains significant amounts of the endotoxin binding/neutralizing protein. The cellular debris was found to have even more activity than lysate itself. By "cell debris" is meant the insoluble material remaining when Limulus amebocytes are lysed by hypotonic shock. It includes nuclei, cell debris and some lysate proteins. The majority is insoluble material. Hypotonic shock may be accomplished by treating the Limulus amebocytes with endotoxin-free distilled water, preferably at 4° C., with shaking (e.g., for 12 h). The mixture is centrifuged, separating the lysate (soluble supernatant) from the cell debris.

The next step is to extract from the cell debris the Limulus amebocyte binding protein. Many solvents have been tested, including water, several alcohols (e.g., methanol, ethanol, isopropanol, and butanol), acetone, chloroform, acetonitrile, acids (e.g., HCl and $H_2SO_4$), bases (e.g., NaOH and ethanolamine), salts (e.g., NaCl), and detergents (e.g., Tween, triton X-100, and SDS). The best results were obtained with denaturants such as urea and guanidine hydrochloride. Surprisingly, six molar solutions of denaturants were effective in extracting the protein without affecting biological activity. This concentration of denaturant would be expected to inactivate most proteins. Thus, the first step in the purification procedure herein is extraction of cellular debris from Limulus amebocyte lysate with a denaturant to produce an extract. The concentration of the denaturant can range from 1M to 10M. A more preferred range would be 3M to 8M. A most preferred concentration is around 6 molar. Urea is the preferred denaturant, because it can be made free of endotoxin by ultrafiltration and it is not readily contaminated by endotoxin containing bacteria.

Preferably, prior to loading the extract onto a cation exchange column, an ultrafiltration step is performed. This step is also accomplished using urea or another denaturant as described above for extraction. In particular, the extract from the cell debris is crudely filtered with a filter aid such as diatomaceous earth (e.g., Celite, Manville Corp.) or one of the cationic or anionic polymeric particles in colloidal suspension (e.g., Biocryl, Supelco division of Rohm and Haas Corp.), then passed through an ultrafiltration membrane. Ultrafiltration membranes may be used in any known form (e.g., plain film, hollow fiber, tubular and spiral) and may be made of any material. Preferred materials are polysulfone, polyvinylidene fluoride, polyacrylonitrile, nylon, or cellulose. Most preferred is a polysulfone, flat or hollow fiber type ultrafiltration membrane. The preferred molecular weight cut-off of the ultrafiltration membrane is 20,000 daltons to 50,000 daltons as can be commercially obtained from Millipore, Filtron or other membrane filter manufacturers. The most preferred membrane has a 30,000 dalton cut-off. The Limulus endotoxin binding/neutralizing protein is now in the filtrate at a very low concentration. The filtrate from the first membrane is concentrated using a second ultrafiltration membrane having a molecular weight cut-off of 5,000 to 10,000 daltons, preferably an 8,000 dalton cut-off membrane. The second ultrafiltration membrane may be the same or different material as the first ultrafiltration membrane, and is preferably made of polysulfone. The principle of operation is the same as the 30,000 cut-off membrane, however, the endotoxin binding/neutralizing protein is now in the retentate with all other proteins greater than e.g., 8,000 daltons.

After the above step, the retentate is subjected to cation exchange chromatography using cellulose, cross-linked agarose or hydrophilic-vinyl polymer resins derivatized with carboxymethyl (CM), Sulphopropyl (SP), Sulphonate (S), or other anionic group. These can be obtained from several manufacturers including Pharmacia (Sephadex®, Sepharose®), Tosoh Corp. (Toyopearl®) or BioRad (Cellex®, Bio-Gel). The most preferred resin is CM-Sepharose®. The pH of loading and elution buffers can range from 4 to 8, with the most preferred range of pH 5 to 5.5. In this step also, urea (or another denaturant as described above for extraction) is an important constituent. All column elution buffers must contain urea (at least about 3 molar) to elute the endotoxin binding protein cleanly from the column.

The elution from the column is accomplished by a step gradient of a salt such as ammonium chloride, potassium chloride or sodium chloride. Sodium chloride is preferred. FIG. 1 shows the results of the CM Sepharose® chromatographic step. The preferred concentration of urea in the eluent used in this step is 1M to 6M. A preferred concentration of urea in this step is 2M to 4M. A most preferred concentration is 2.5M to 3.5M. When sodium chloride is used in the eluant, biological activity elutes at a concentration of sodium chloride of from around 0.5 to 1 molar.

Figure 2:
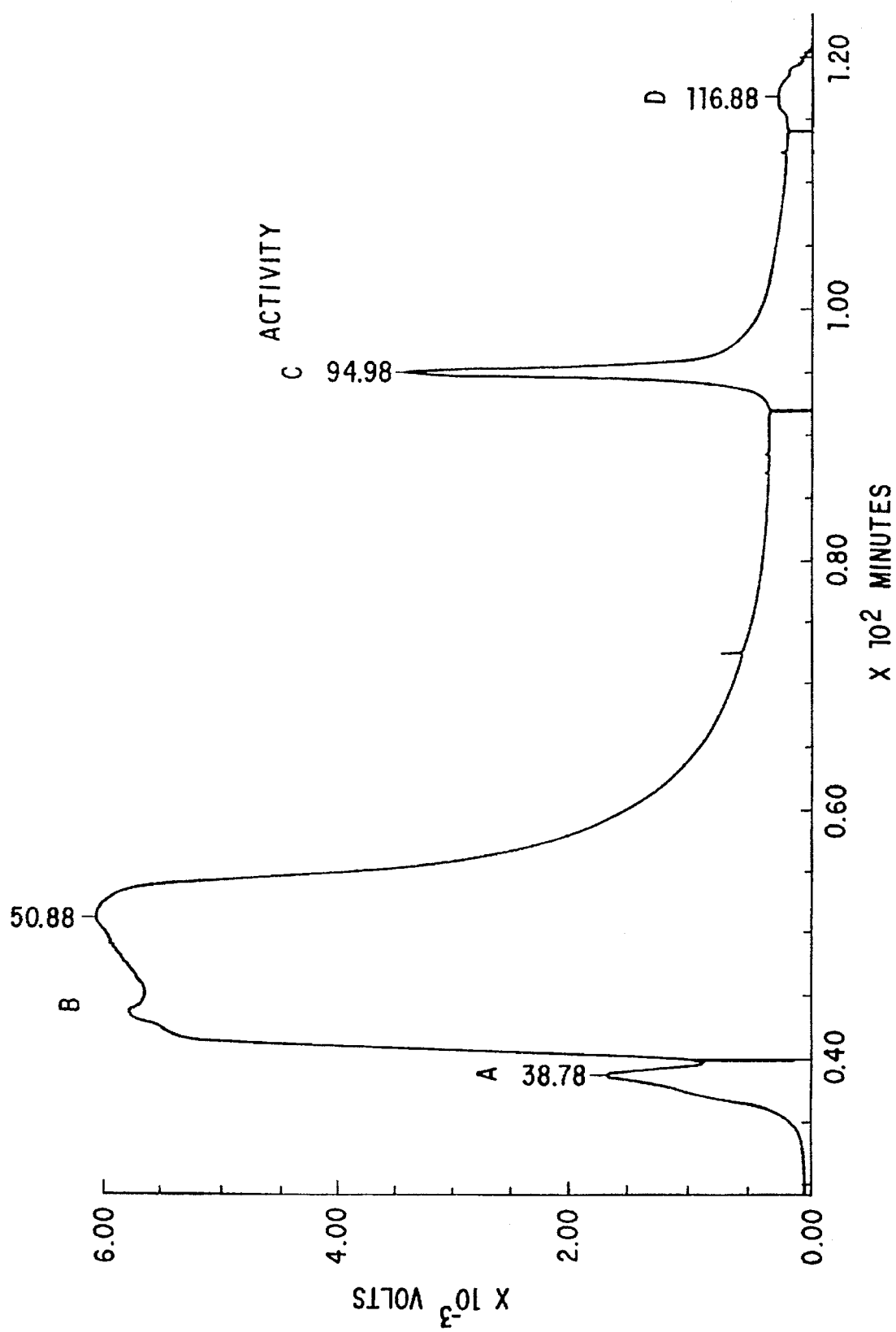
FIG. 2 shows reversed phase chromatographic purification of Peak −1) from FIG. 1. Peak A: 25% isopropanol (IPA) elution, Peak 3: 0.35% IPA elution, Peak C: 50% IPA elution, Peak D: column wash with 100% IPA.

After the cation exchange step, the salt-eluted peak of activity is applied to a reversed-phase column. The preferred method employs a resin having 4, 8, or 18 carbon chains (C-4, C-8 or C-18, respectively). The most preferred method employs a C-4 resin commercially available from such resin manufacturers as Vydac, Waters, Tosoh Corp., etc. The protein is eluted by a step gradient of, for example, isopropanol and trifluoroacetic acid (TFA). The concentration of trifluoroacetic acid is ideally 0.2%, but can range from 0 to 0.4%, preferably 0.15 to 0.25%. FIG. 2 shows the location of the activity during treatment on the reversed-phase column. The reversed-phase column step effects desalting and further purifies the material to virtual homogeneity. The Limulus protein is remarkably stable to the organic solvents and low pH of this column. The protein is stable over a pH range of 1-3 in the presence of TFA. The material may now be lyophilized. The purified Limulus protein has an isoelectric pH (pI), which is greater than 10, indicating a very basic protein. The molecular weight of the protein as determined by SDS-PAGE is 12,500±100. The first three N-terminal amino acids of this purified material are Asp-Gly-Ile This protein is the preferred protein used in accordance with the present invention. Its amino acid sequence is set forth in FIG. 15 where it is identified as SEQ. ID. NO. I.

The inventors have also discovered a domain, within this endotoxin binding/neutralizing protein, necessary for endotoxin binding/neutralization. This domain comprises the amino acid sequence of from amino acid position 30 to amino acid position 55 set forth in FIG. 15. Thus in a preferred embodiment, the present invention uses a protein corresponding at least to that portion of, SEQ. ID. NO. I or III corresponding to amino positions 30 to 55 and up to complete SEQ. ID. NO. I or III where the components attached to the amino end or the carboxyl end of the domain may be independently present at varying lengths.

It should be noted that Watson and Sullivan, U.S. Pat. No. 4,107,077, teaches that there is an increase in sensitivity of the lysate by organic extraction with chloroform. It appeared logical that a protein which inactivated endotoxin would appear as an inhibitor in the endotoxin assay. Thus, it was hoped that the protein was the inhibitor which is extracted into chloroform and could be recovered from that extract. However, surprisingly, this was not successful. Since the protein is fairly hydrophobic, it may be in the organic extract, but denatured in some way.

The majority of the purified material had an amino acid sequence which appears to be identical to a protein from Limulus that was isolated by Tanaka et al. The material was subsequently purified by Iwanaga et al, as reported in the International Symposium on Pyrogen, held Jun. 23–26, 1987 in China. However, in the latter case, a different purification procedure was employed.

In addition to a protein having an apparently identical amino acid sequence to that reported in Iwanaga et al, some related proteins were also purified, which have different amino acid sequences. These variant proteins have not previously been described. In a first protein, on the N-terminal thereof, a serine rather than an aspartic acid residue is located. Furthermore, an asparagine is located in the second position from the N-terminal rather than a glycine as reported in Iwanaga et al. Therefore, a protein having an initial amino acid sequence of Ser-Asn is also part of the present invention. Other possible protein derivatives are those beginning with Asp-Asn- Ser-Gly-, and Ser-Asn-, and also a protein having an N-terminal asparagine with one less amino acid than the natural sequence. Each of these variant proteins is also part of the present invention, and they may be used in each aspect of the invention described hereinbelow. They will be referred to as endotoxin binding/neutralizing protein variants (or variant proteins for short), as distinguished from the natural sequence endotoxin binding protein, which is the protein having the amino acid sequence reported in Iwanaga et al.

The variant proteins were not separated from each other. Rather, upon sequencing the most purified samples, some positions were uniformly one amino acid, while other positions showed major variation. This is interpreted as a mixture of proteins showing microheterogeneity. It is consistent with the existence of a gene family for these proteins individual gene sequences are very homologous, but not identical. It remains to be seen if their individual specific activities vary significantly.

The present invention also encompasses DNA sequences which encode the polypeptides of the present invention, particularly those encoding at least the domain of from amino acid position 30 to 55 of SEQ. ID. NO. I or III and up to the whole SEQ. ID. NO. I or III, vectors containing these DNA sequences, and microorganisms such as E. coli, yeast, etc., transformed with the vectors. The transformed microorganisms can be used to produce large quantities of the polypeptide materials, including the variant proteins described above. The genes of this invention may be altered so as to maximize codon expression in a given host.

The DNA sequences used in accordance with the present invention may be obtained in any manner known in the art, such as cloning and/or DNA synthesis. Various methods for synthesizing both DNA and RNA sequences are discussed in "Synthesis and Applications of DNA and RNA", edited by S. A. Narang, Academic Press Inc. (1987), which is hereby incorporated by reference. Once obtained these gene sequences may be expressed in microorganisms using known methodology. See, e.g., Maniatis et al, "Molecular Cloning: A Laboratory Manual" Cold Spring Harbor Laboratory (1982), which discusses cloning and expression methodologies and which is hereby incorporated by reference.

In accordance with the preferred embodiment of the present invention, a protein encoded by SEQ. ID. NO. III is produced in a yeast host where it may be produced as a glycoprotein comprising the amino acid sequence of the endotoxin binding protein of the present invention (SEQ. ID. NO. I) to which the tetrapeptide "Glu-Ala-Glu-Ala" is covalently attached to the amino terminal of the endotoxin binding protein. This glycoprotein encoded by SEQ. ID. NO. II is excreted by the yeast host.

Procedure for Assaying for Endotoxin Binding Activity

Figure 3:
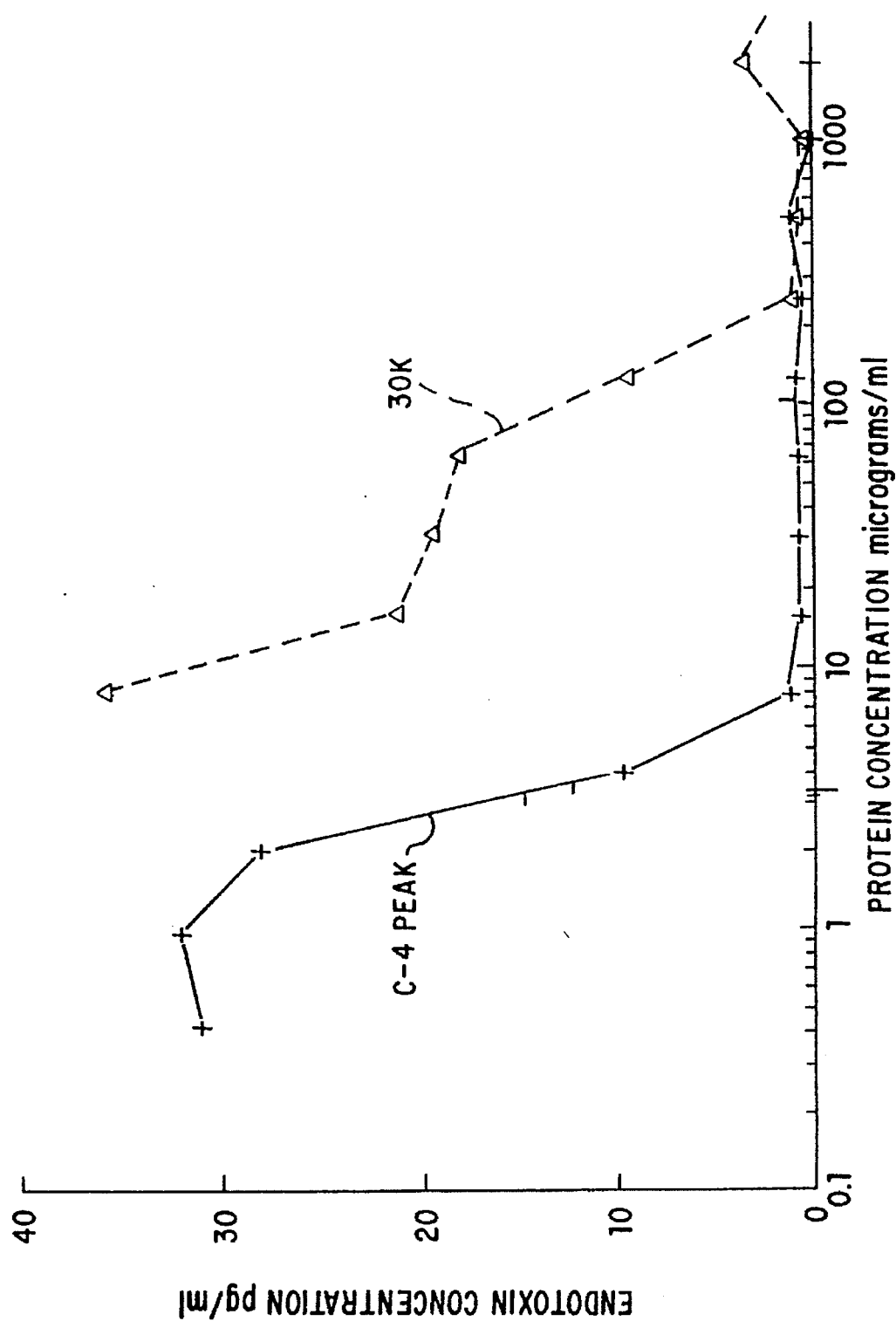
FIG. 3 is a plot of apparent endotoxin concentration (measured by LAL) versus protein concentration. Such a plot can be used to assess protein specific endotoxin inactivating/neutralizing activity. Specific activity is expressed as the amount of protein needed to achieve 50% reduction of endotoxin activity in the assay system (5 nanograms of endotoxin Per 100 microliters). For convenience, units are expressed as micrograms protein×$10^5$ needed to reduce 5 nanograms activity/100 microliters of standard endotoxin by 50%.
Figure 4:
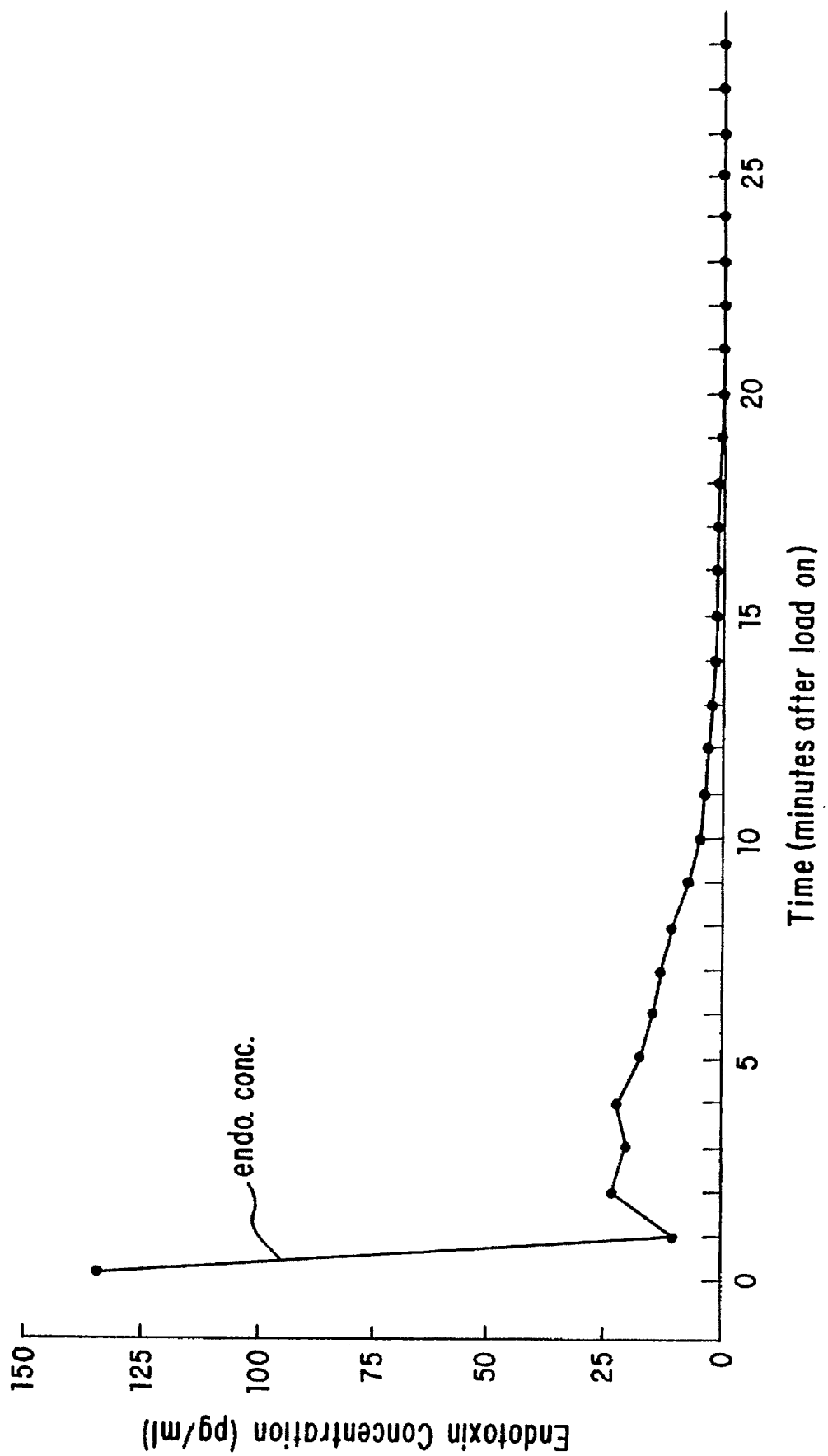
FIG. 4 shows endotoxin removal by affinity chromatography with endotoxin binding/neutralizing protein immobilized to a solid support.

To follow the purification of the endotoxin binding/neutralizing protein during the above purification steps, assays can be performed in solution. One publication describing typical assays for $LR_{50}$ values is Novitsky et al, J. Clin. Microbiol. pp. 211–216 (1985). A specific procedure follows:

A 96-well microtiter plate is used. Protein fractions are serially diluted across the top row and mixed with a standard endotoxin solution. There is another series of dilutions done on all samples to get within range of the assay, but basically the endotoxin recovered in the well after mixing with a suspected endotoxin inactivating protein is measured. This is compared to negative controls and an endotoxin standard curve. It is found that the added endotoxin is inactivated at the high protein concentrations. As the protein is diluted across the plate, a point is reached where it is too dilute to inactivate the added endotoxin. This dilution is a measure of the protein specific activity. FIG. 3 represents a graphical form of such experiments. In FIG. 3, the dotted curve represents the crude extract after ultrafiltration, and the solid line is the most highly purified fraction from the reversed-phase column.

In Vivo Activity of the Endotoxin Binding/Neutralizing Protein of the Present Invention The endotoxin binding protein of the present invention (and variants thereof) may be incubated with endotoxin, and then administered to animals, and the bound endotoxin is not found to cause any pyrogenicity in vivo. The details of the endotoxin test are presented hereinbelow in the examples section.

Surprisingly, and even less predictably, the present endotoxin binding protein may be administered to an animal after the animal has already been exposed to endotoxin, and the endotoxin binding protein can reverse the effects of free endotoxin in vivo. Moreover, the endotoxin binding/neutralizing protein may be administered to an animal before contact with endotoxin by the animal, and the endotoxin binding/neutralizing protein will exert a protective effect against the effects of endotoxin. Accordingly, the endotoxin binding/neutralizing protein of the present invention may be formulated into a pharmaceutical composition for treating an animal in vivo, so as to exert a therapeutic effect if endotoxin is present in the animal, or to exert a protective or preventive effect, if the animal should come into contact with endotoxin later. Details on the experimental tests showing the in vivo effects of the endotoxin binding/neutralizing protein of the present invention are also presented in the examples section hereinbelow.

It should be noted that in vivo activity of this type would have been unpredictable based on the bare disclosure of the in vitro endotoxin binding/neutralizing capability of this protein. According to Nachum (described above), there were two possibilities for the removal of endotoxin by lysate proteins, binding or enzymatic cleavage of endotoxin. The inventors looked for degradation products and found none (specifically, free fatty acids that could have been released by esterases). Subsequent work has found binding to be the mechanism. It is more expected that the endotoxin would be inactivated in vivo by an enzymatic action the molecule would be structurally different. However, by only binding, one would assume the entire endotoxin structure would still be present and available to trigger the normal biological response to the toxin. The noted inactivation in vitro might easily have been an artifact of an artificial assay system—perhaps a conformational change in the bound endotoxin not reacting with the LAL reagent, or it is also possible that the Limulus endotoxin binding protein was inhibiting the clotting reaction by itself (since it is present in lysate, this possibility is hard to rule out without the in vivo results).

Although it might be possible for the endotoxin binding protein of the present invention to be administered in vivo without any additives thereto, it is preferably mixed with a carrier, and if necessary, other adjuvants.

By the term "carrier" as used herein is meant a synthetic or natural, inorganic or organic substance which is added to the endotoxin binding protein of the present invention to assist the active ingredient in reaching the location to be treated therewith and to facilitate storage, transportation and handling of the active ingredient.

Among suitable livid carriers, there may be included aromatic hydrocarbons such as benzene, toluene, xylene, cumene, etc., paraffinic hydrocarbons such as mineral oil and the like, halogenated hydrocarbons such as carbon tetrachloride, chloroform, dichloroethane and the like, ketones such as acetone, methyl ethyl ketone, etc., ethers such as dioxane, tetrahydrofuran and the like, alcohols such as methanol, propanol, ethylene glycol and the like, dimethyl formamide, dimethylsulfoxide, water, etc. Mixtures of any number of liquid carriers are also envisioned. Upon dissolution of lyophilized active ingredient with unbuffered pyrogen free distilled water or saline or phosphate buffered saline (pH 6.5 to 7.5), the protein is not completely soluble. In order to avoid undesirable physiological side-effects which might result from such suspensions, the pH may be adjusted to slightly alkaline pH (pH 8 to 9) at which the material becomes water clear. For this reason, the most preferred liquid carrier is pyrogen free distilled water or saline adjusted to an alkaline pH.

In order to enhance the effectiveness of the compound according to this invention, it is possible to use such adjuvants as given below either singly or in combination in accordance with the purpose of each application thereof while taking into consideration the form of their preparation and their field of application.

Namely, exemplary adjuvants may include anionic surfactants such as alkyl sulfates, aryl sulfonates, succinates, polyethylene glycol alkyl aryl ether sulfates, and the like, cationic surfactants such as alkylamines, polyoxyethylene alkylamines, etc., non-ionic surfactants such as polyoxyethylene glycol ethers, polyoxyethylene glycol esters, polyol esters and the like, and amphoteric surfactants. Encapsulation or microencapsulation of the active ingredient in liposome vesicles is also within the scope of this invention.

Examples of stabilizers, thickeners, lubricants and the like are isopropyl hydrogen-phosphate, calcium stearate, wax, casein, sodium alginate, serum albumin, other blood proteins, methylcellulose, carboxymethylcellulose, gum arabic, etc. It should be kept in mind that these ingredients are not limited to the recited examples.

The active materials according to the present invention can be administered by any route, for example, orally, parenterally, intravenously, intradermally, subcutaneously, or topically, in liquid or solid form. Preferably, the route of administration is intravenously.

The solutions or suspensions may also include the following components: a sterile diluent such as water for injection, saline solution, oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple base vials made of glass or plastic.

While dosage values will vary with the specific severity of the disease condition to be alleviated, good results are achieved when the compounds described herein are administered to a subject requiring such treatment as an effective oral, parenteral or intravenous dose of from 100 to 10,000 units per nanogram of measured endotoxin per day per patient. A particularly preferred effective amount is about 1000 to 5000 units per nanogram of measured endotoxin per day per patient. Most preferred is the administration of 0.1 to 100 mg of endotoxin binding protein/kg of body weight per day per patient. It is to be understood, however, that for any particular subject, specific dosage regimens should be adjusted to the individual need and the professional judgment of the person administering or supervising the administration of the aforesaid compound. It is to be further understood that the dosages set forth herein are exemplary only and they do not limit the scope or practice of the invention. The dosages may be administered at once, or may be divided into a number of smaller doses to be administered at varying intervals of time.

Specific diseases which could be treated include septicemia, toxic shock, and any other condition, especially gram-negative bacterial infections, which is accompanied by an increase in in vivo endotoxin content. Other examples are endotoxin-related arthritis, gonorrhea, periodontal disease, spinal meningitis, and infections of amniotic fluid.

Although this invention and its preferred embodiments are primarily addressed to use in humans, veterinary use is also encompassed by the invention. In this regard, the active ingredient may be administered to reduce or prevent the pyrogenic or other ill effects of endotoxin in vivo in, for example, dogs, cats, horses, cattle, sheep, and rabbits. Administration to laboratory animals, such as mice and rats, in order to prevent or reduce effects of endotoxin, is also contemplated.

Although polyclonal and monoclonal antibodies to endotoxin have also been developed for this purpose and are the subject of ongoing development, the endotoxin binding protein of the present invention has advantages over antibodies which make it a preferred candidate for a therapeutic. The binding constant is very high and its low molecular weight may be less antigenic. In a recent paper, Greisman and Johnston, J. Infect. Disease 157:54–64 (1988), it has been shown that at least one anti-serum against endotoxin is ineffective in reducing the effects of endotoxin in vivo. In contrast, the in vivo experiments in the present invention have shown that the endotoxin binding protein may inactivate endotoxin in both rabbit and human serum.

Removal of Endotoxin From Solutions

Endotoxin contamination of pharmaceuticals is a problem toward which many removal protocols have been directed. Many of these are summarized in Biopharm, April, 1988, pages 22–29, and the references cited therein. They all fall short when the contaminated material is or contains a high molecular weight substance, such as protein. Most of the existing technology for endotoxin removal (ultrafiltration, ion exchange, affinity chromatography) does not separate protein and endotoxin. The present invention involves using the endotoxin binding protein (e.g., from Limulus) as an immobilized affinity ligand to achieve this separation. The preferred solid support for covalently coupling the endotoxin binding protein is cellulose, agarose or other hydrophilic polymer derivatized to contain carboxyl, hydroxyl, amino, epoxide or other chemically reactive group to which proteins may be covalently attached using well known coupling chemistry. These methods include using water soluble carbodiimide or carbonyldiimidazole, glutaraldehyde, etc. The most preferred support is the hydrophilic vinyl polymer in pellicular or membrane form containing carboxy-methyl groups activated with water-soluble carbodiimide. The inventors have attached the binding protein covalently to chromatographic beads and the protein retains its biological activity. Furthermore, by mixing the beads with endotoxin contaminated proteins, the solution could be detoxified. This was done by mixing the beads in batch mode in test tubes, or by packing a column with the beads and passing the solutions over it.

Figure 5:
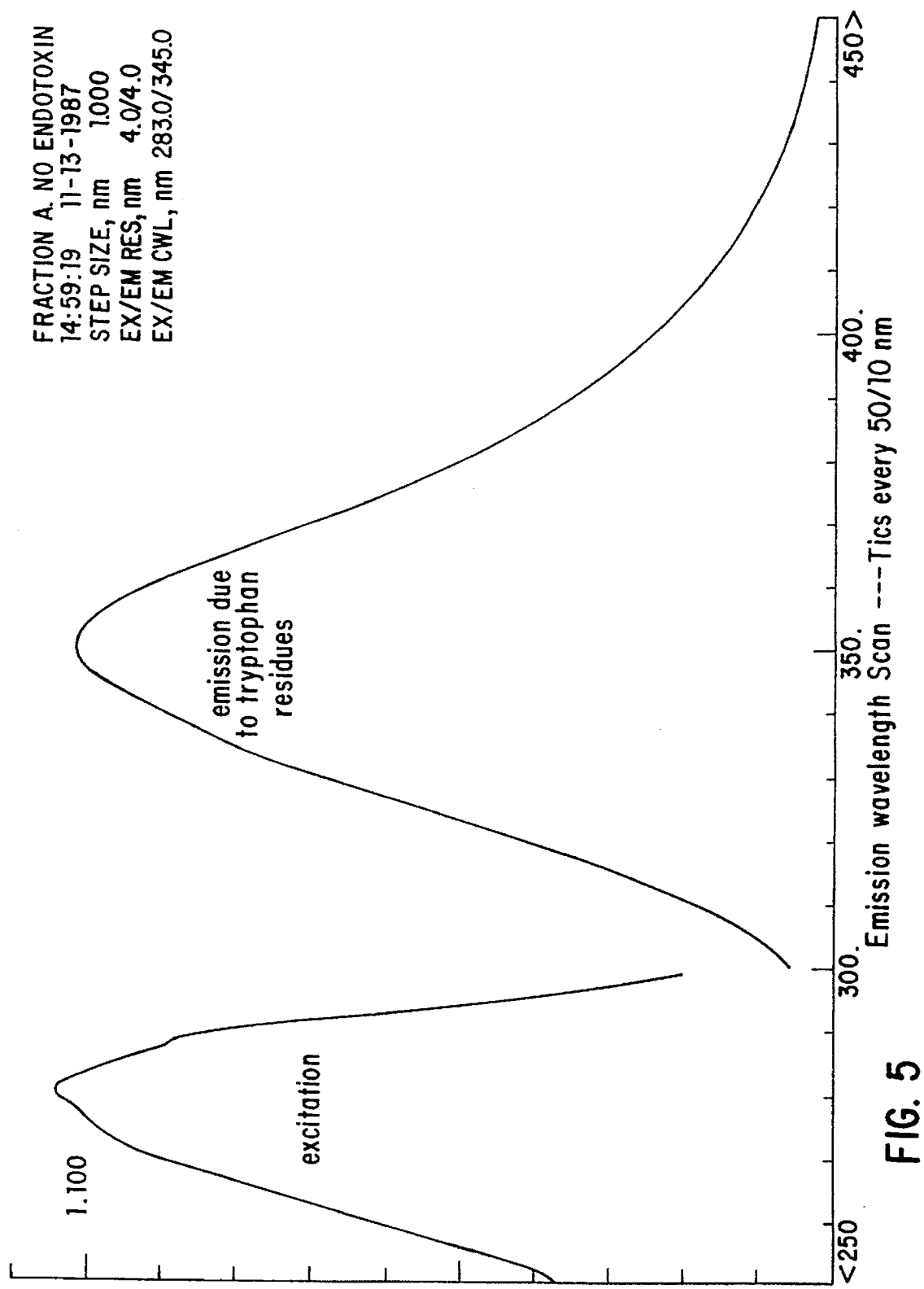
FIG. 5 shows fluorescence excitation and emission spectra of Limulus endotoxin binding/neutralizing protein.

The protein could also be covalently attached to filter membranes for the same purpose. FIG. 5 shows an experiment with such a filter. A 40 ml solution containing approximately 130 pg/ml endotoxin was recirculated through a filter containing the binding protein. There was an initial large drop in the toxin concentration that was further reduced as the material recirculated.

The present inventors further conducted a direct comparison of two immobilized polymyxin resins compared to the present ligand on similar gel particles. The experiment took 100 microliter gel volumes of each in a microcentrifuge tube and added 100 nanograms of E. coli endotoxin in 1 ml of various solutions to each. The tubes were mixed end over end for one hour. In 10 mM Tris, all three performed equally well. In 25% human serum albumin (HSA) and 5% HSA, the present endotoxin binding protein was able to remove significantly more endotoxin. Interestingly, in distilled water, polymyxin was superior. Thus, the present endotoxin binding protein exhibits surprisingly superior performance in protein-containing solutions. Other possible proteins contaminated by endotoxin are HSA, interferon, interleukins, growth factors, hormones, proteases, TPA, TNF, monoclonals, EGF, insulin, and erythropoietin.

Extracorporeal Treatment of Septic Shock

Because of the ability of the endotoxin protein to function in protein solutions and human serum, an affinity membrane or hollow fiber may be constructed for the purpose of removing endotoxin from the blood of patients extracorporeally. In such a mode, similar to kidney dialysis, blood containing elevated concentrations of endotoxin from a variety of potential clinical conditions is circulated through an affinity device such that the serum is brought into direct contact with endotoxin binding protein covalently bound to the membrane. Since the amount of endotoxin binding protein being released into the general circulation is much reduced from an intravenous application, potential side effects are minimized.

Figure 6:
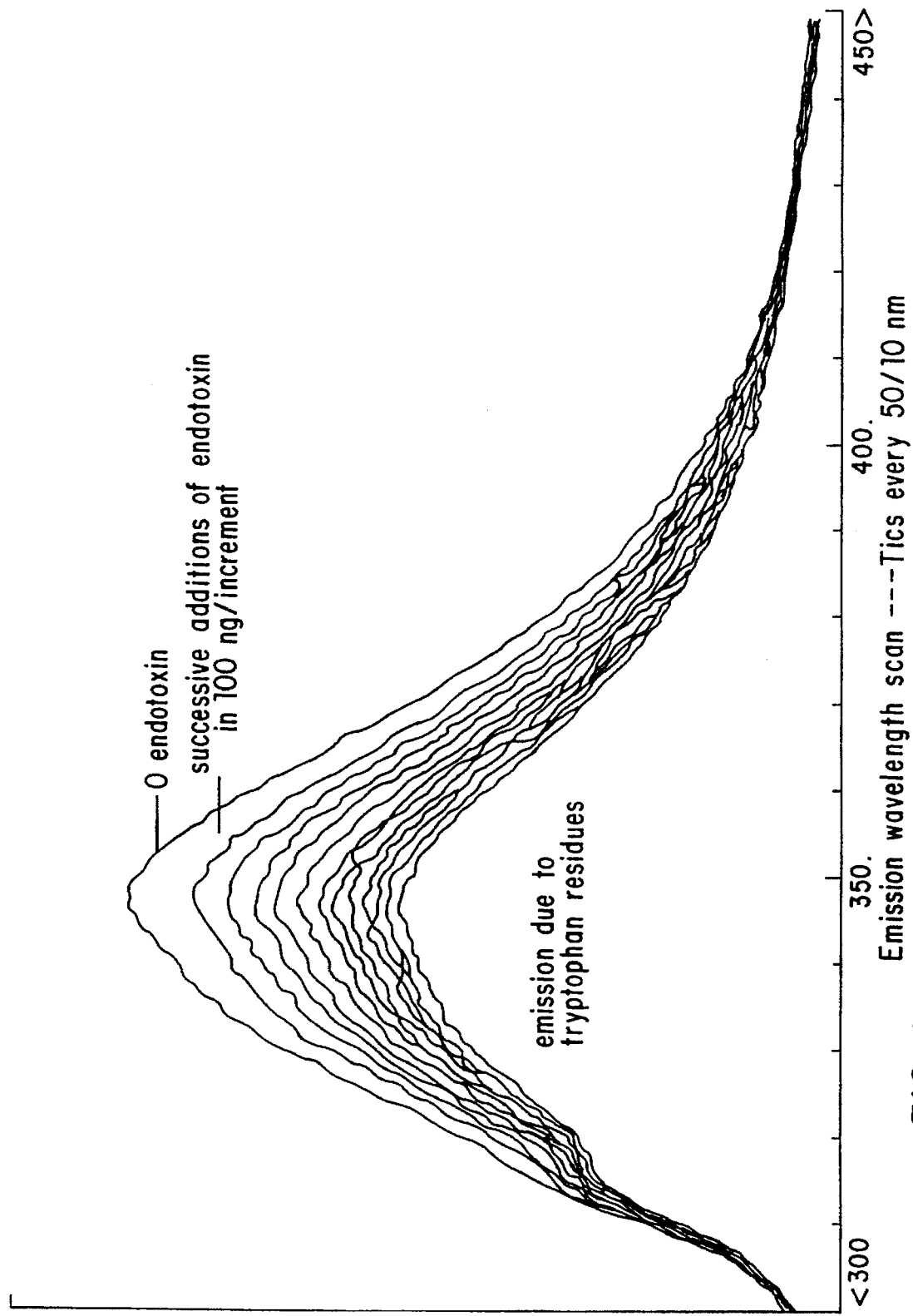
FIG. 6 shows successive decreases in the emission spectra of Limulus endotoxin binding/neutralizing protein upon successive additions of endotoxin.

Assay for Binding Affinity and Application of the Endotoxin Binding/Neutralizing Protein in an Alternative Endotoxin Assay A known optical property of all proteins is the ability of some aromatic amino acids to fluoresce when excited at certain wavelengths. The present inventors looked specifically at tryptophan residues. These are excited at around 283 nm and fluoresce at around 350 nm. See FIG. 6.

Figure 7:
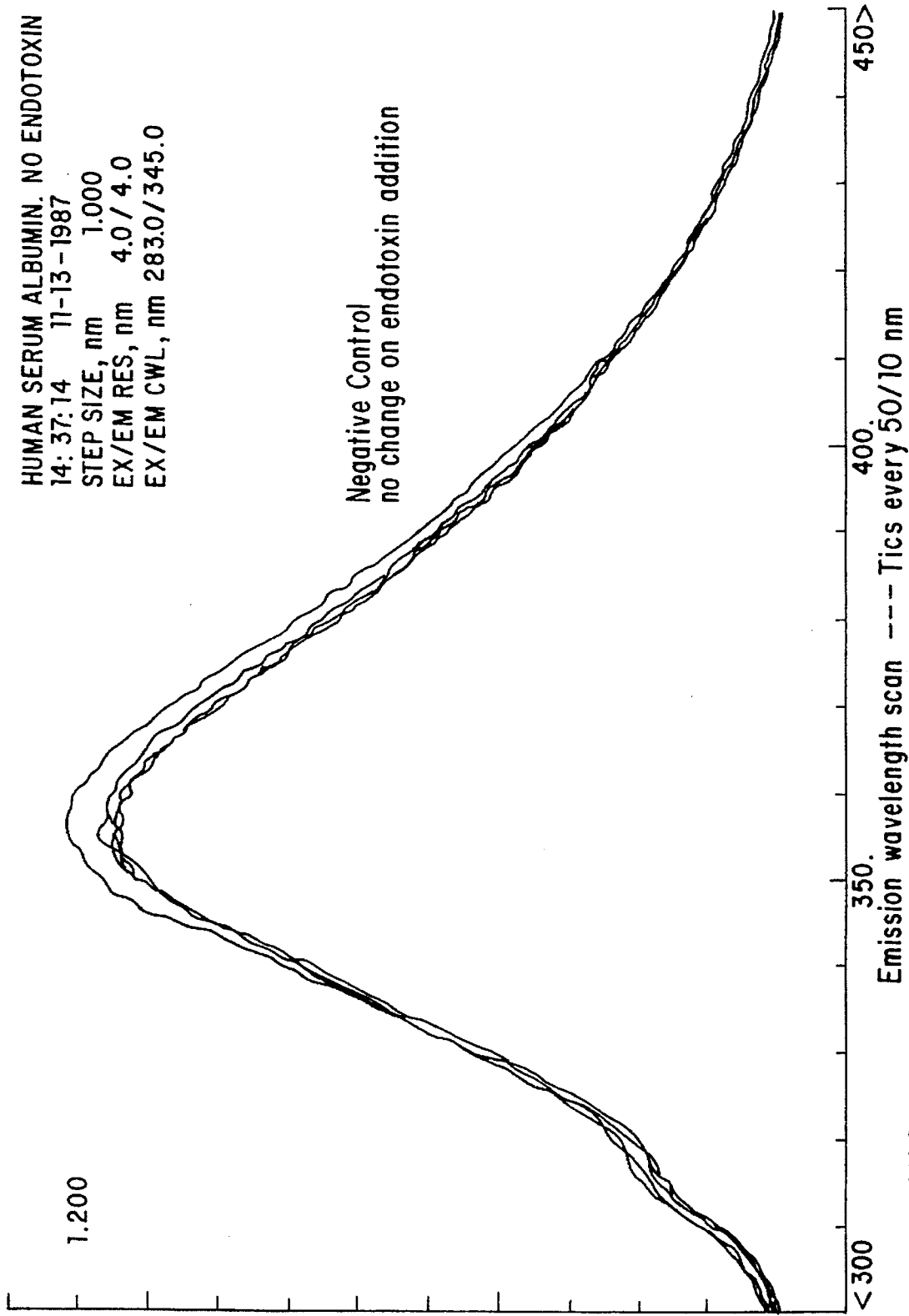
FIG. 7 shows lack of successive decreases in the emission spectra of human serum albumin upon successive additions of endotoxin (negative control).
Figure 8:
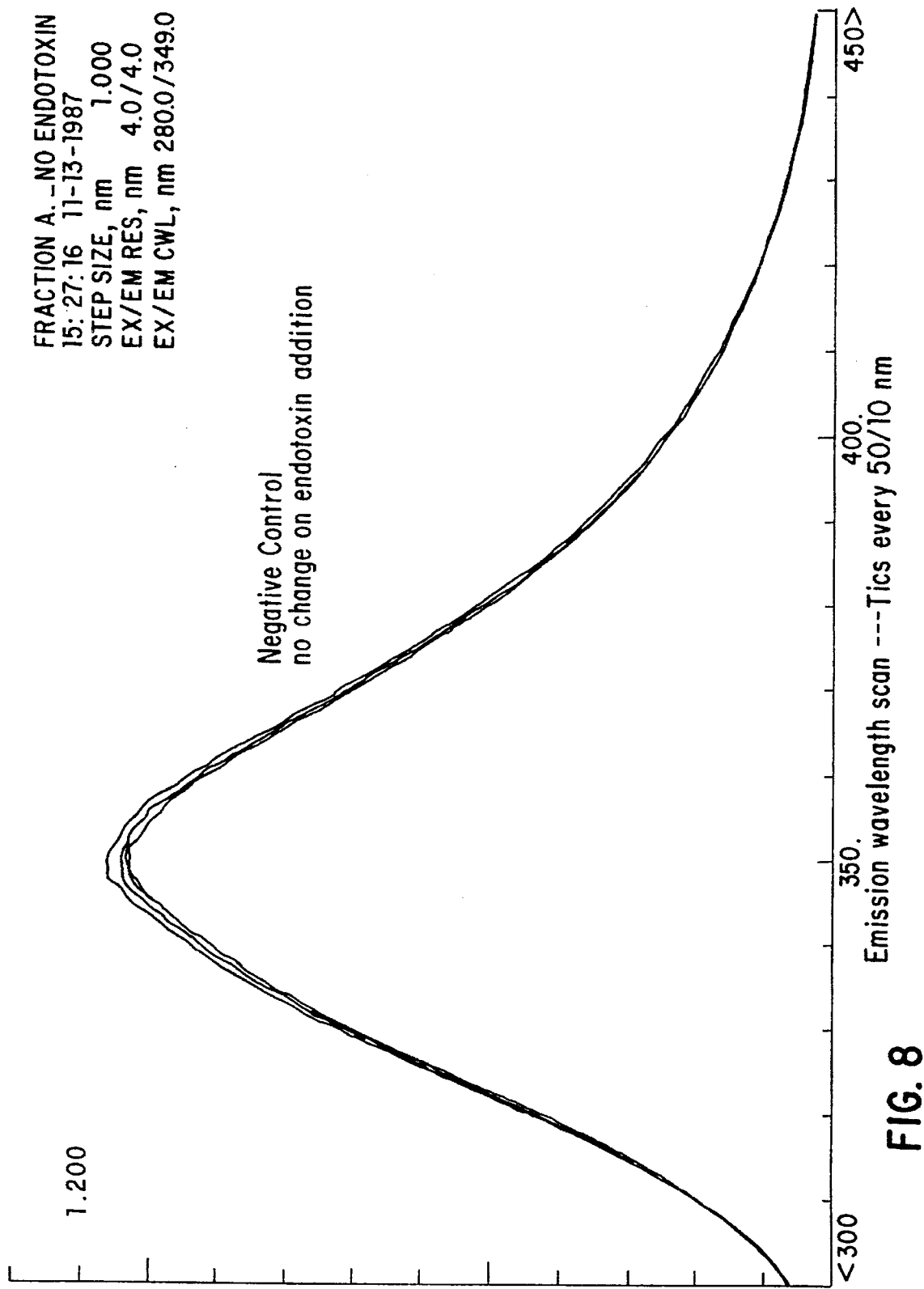
FIG. 8 shows lack of successive decreases in the emission spectra of peak B, FIG. 2 upon successive additions of endotoxin (negative control).
Figure 9:
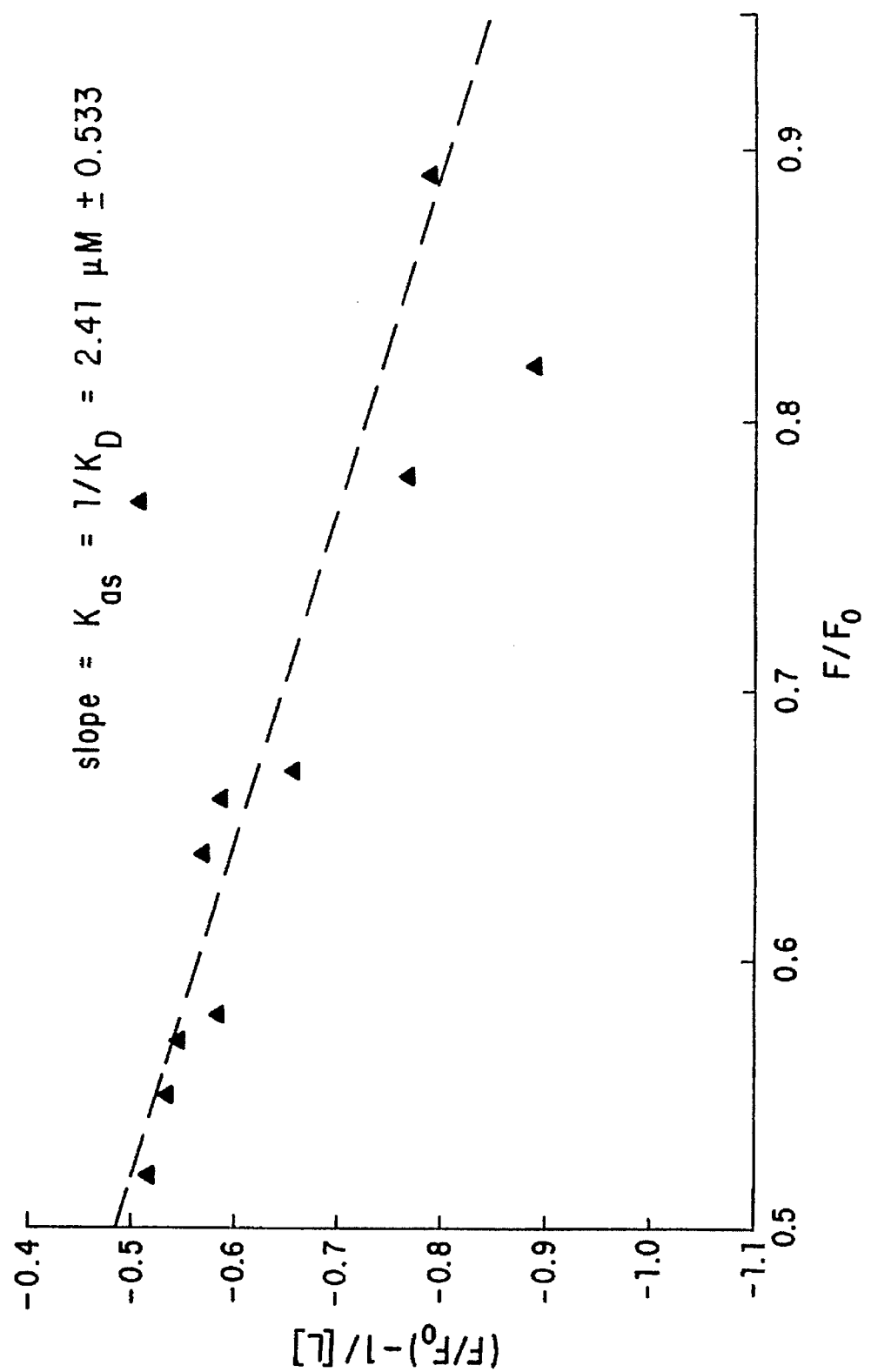
FIG. 9 shows a fluorescence titration of Limulus endotoxin binding/neutralizing protein at pH 3.86. $K_D=2.41$ micromolar.
Figure 10:
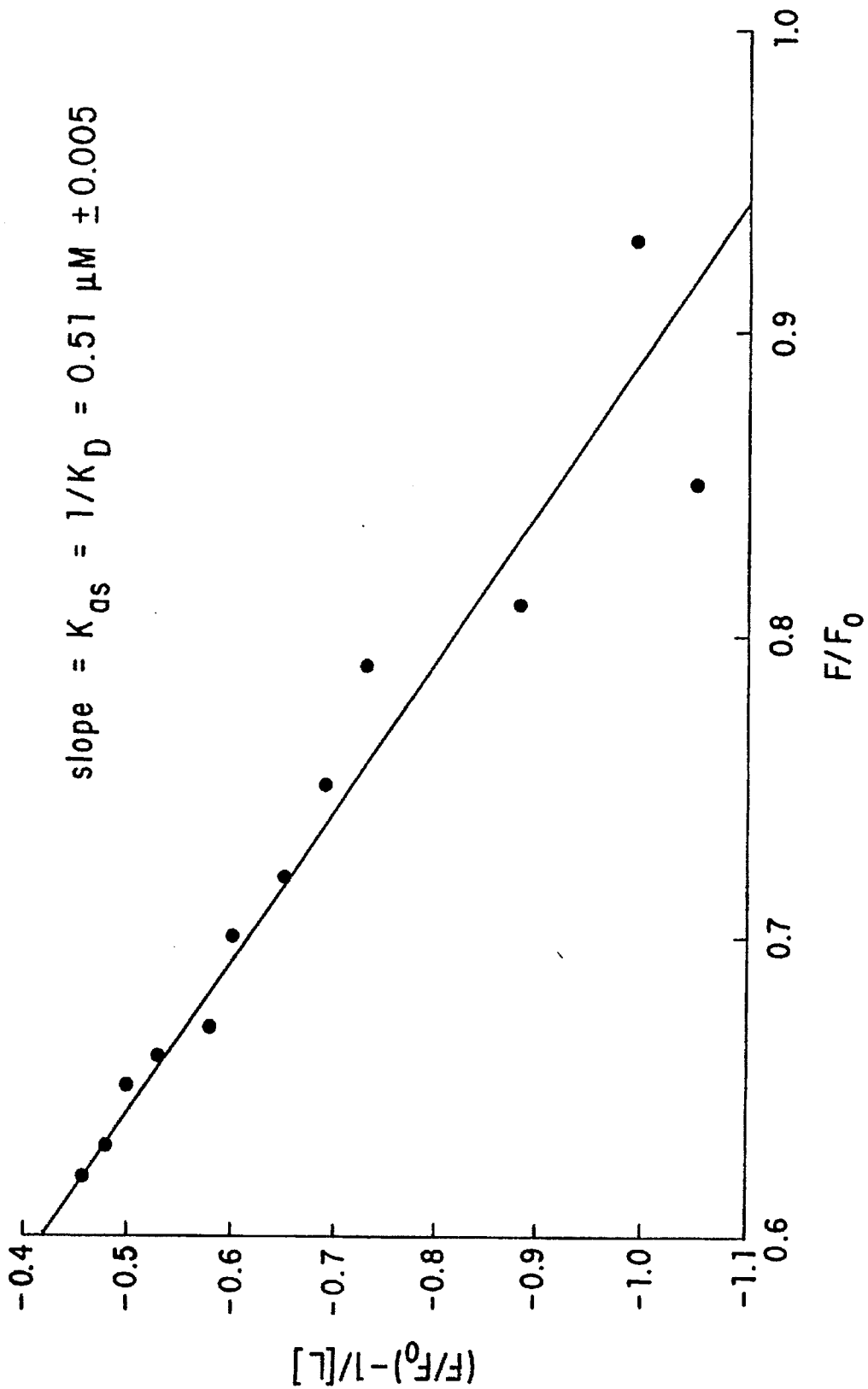
FIG. 10 shows fluorescence titration of Limulus endotoxin binding/neutralizing protein at pH 6.91. $K_D=0.51$ micromolar.
Figure 11:
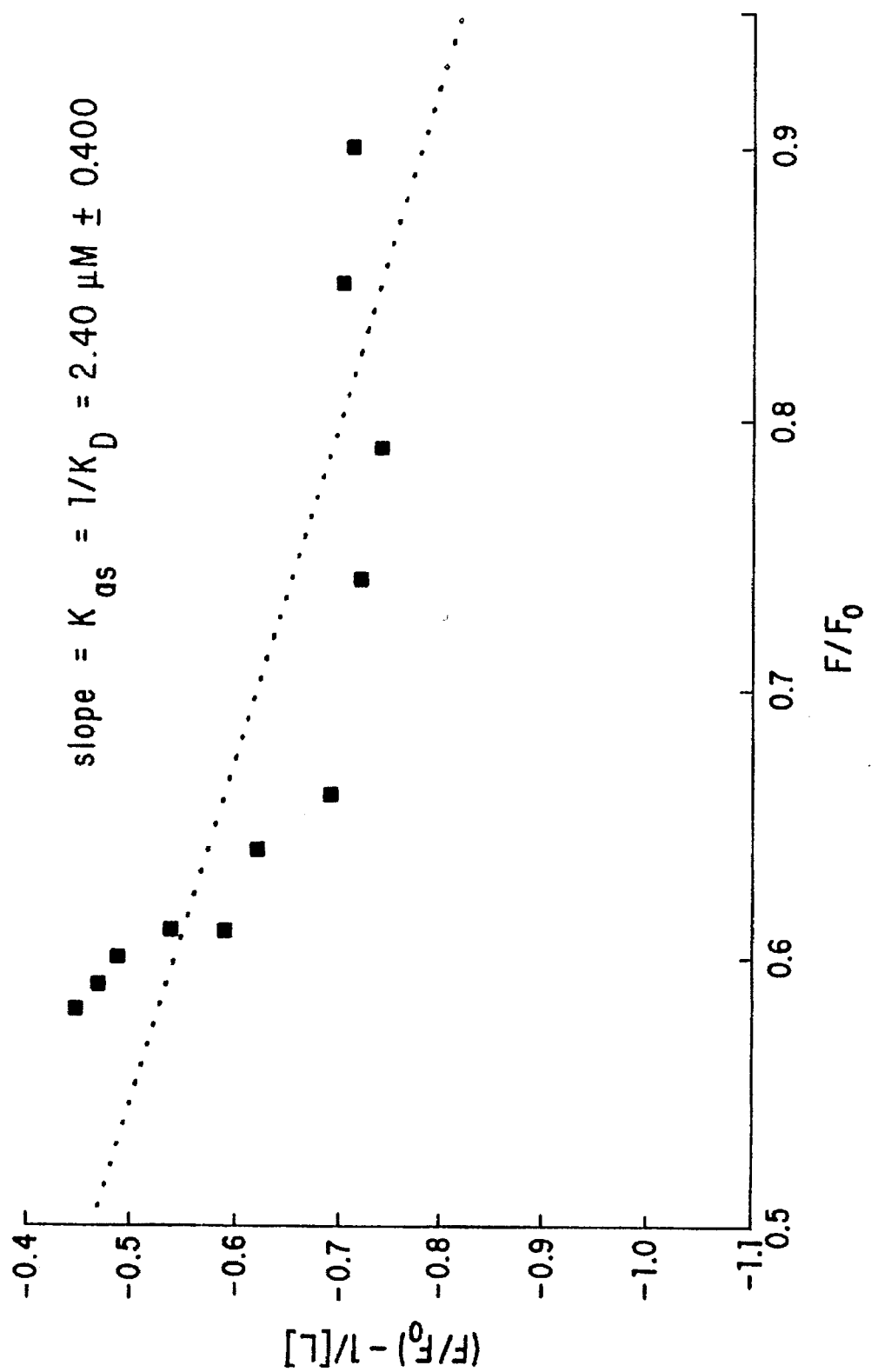
FIG. 11 shows fluorescence titration of Limulus endotoxin binding/neutralizing protein at pH 8.80. $K_D=2.40$ micromolar.
Figure 12:
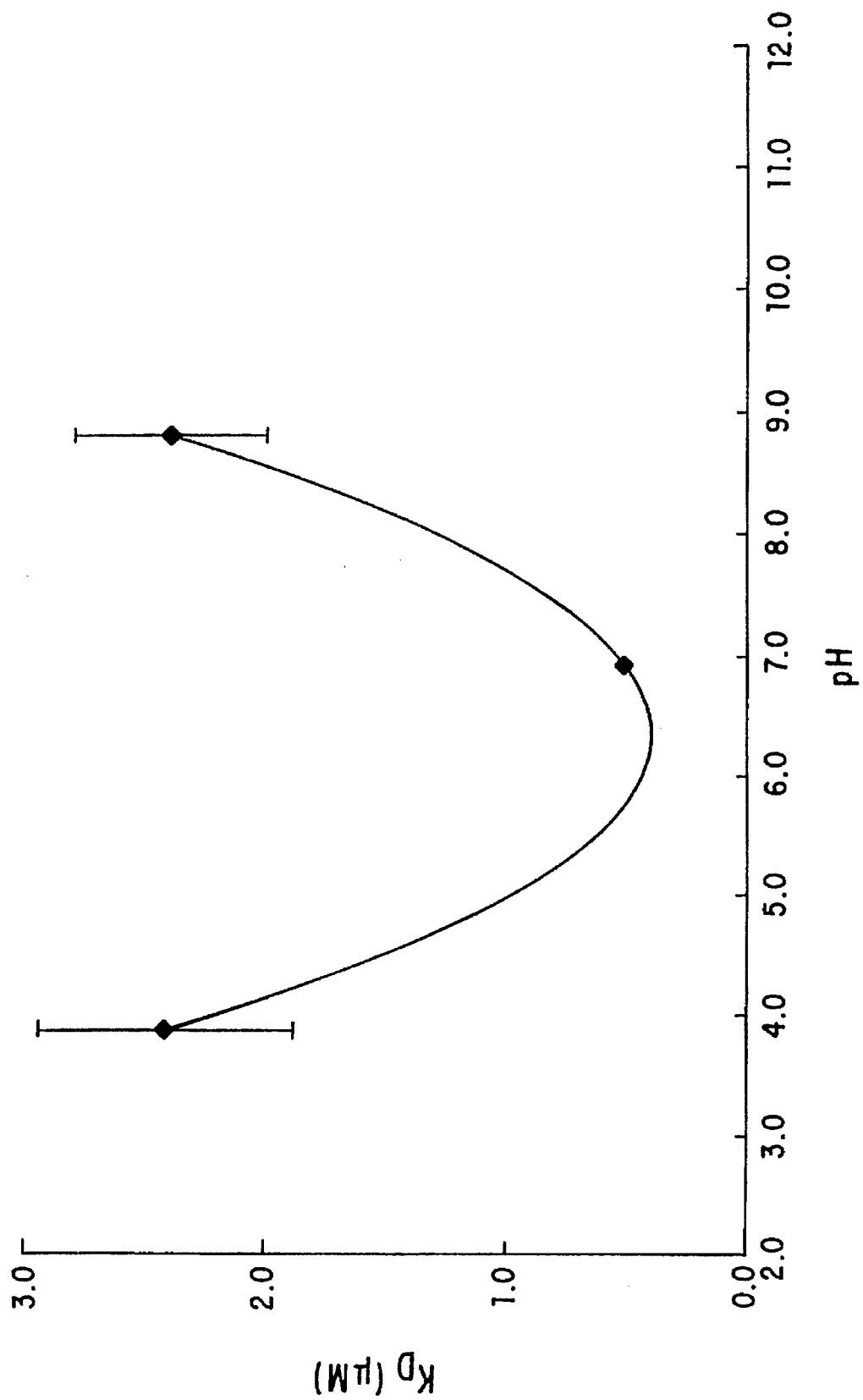
FIG. 12 shows the effect of pH on dissociation constant of Limulus endotoxin binding/neutralizing protein.
Figure 13:
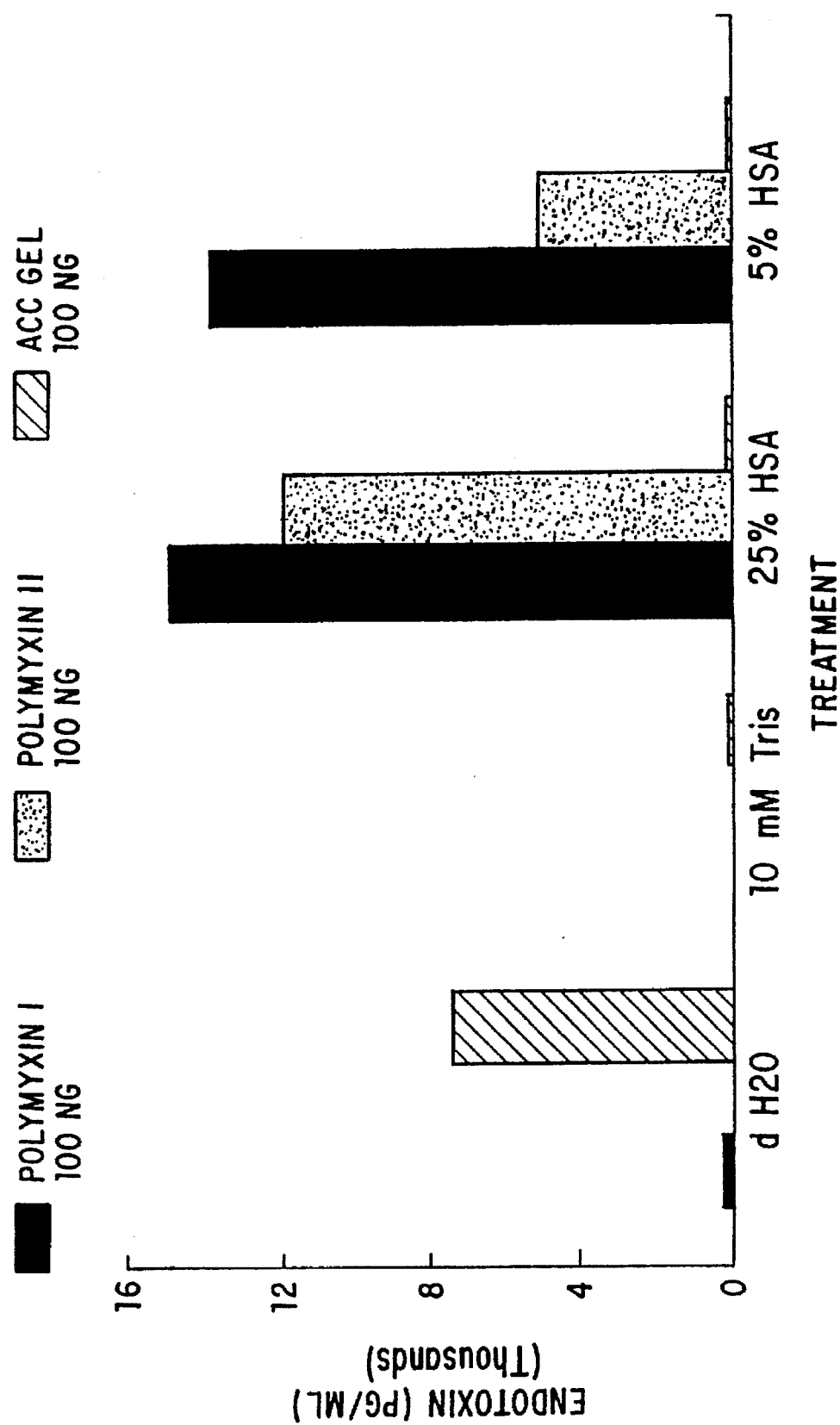
FIG. 13 is a comparison of immobilized Limulus endotoxin binding/neutralizing protein compared to two immobilized polymyxin resins in proteinaceous and non-proteinaceous solutions.
Figure 14:
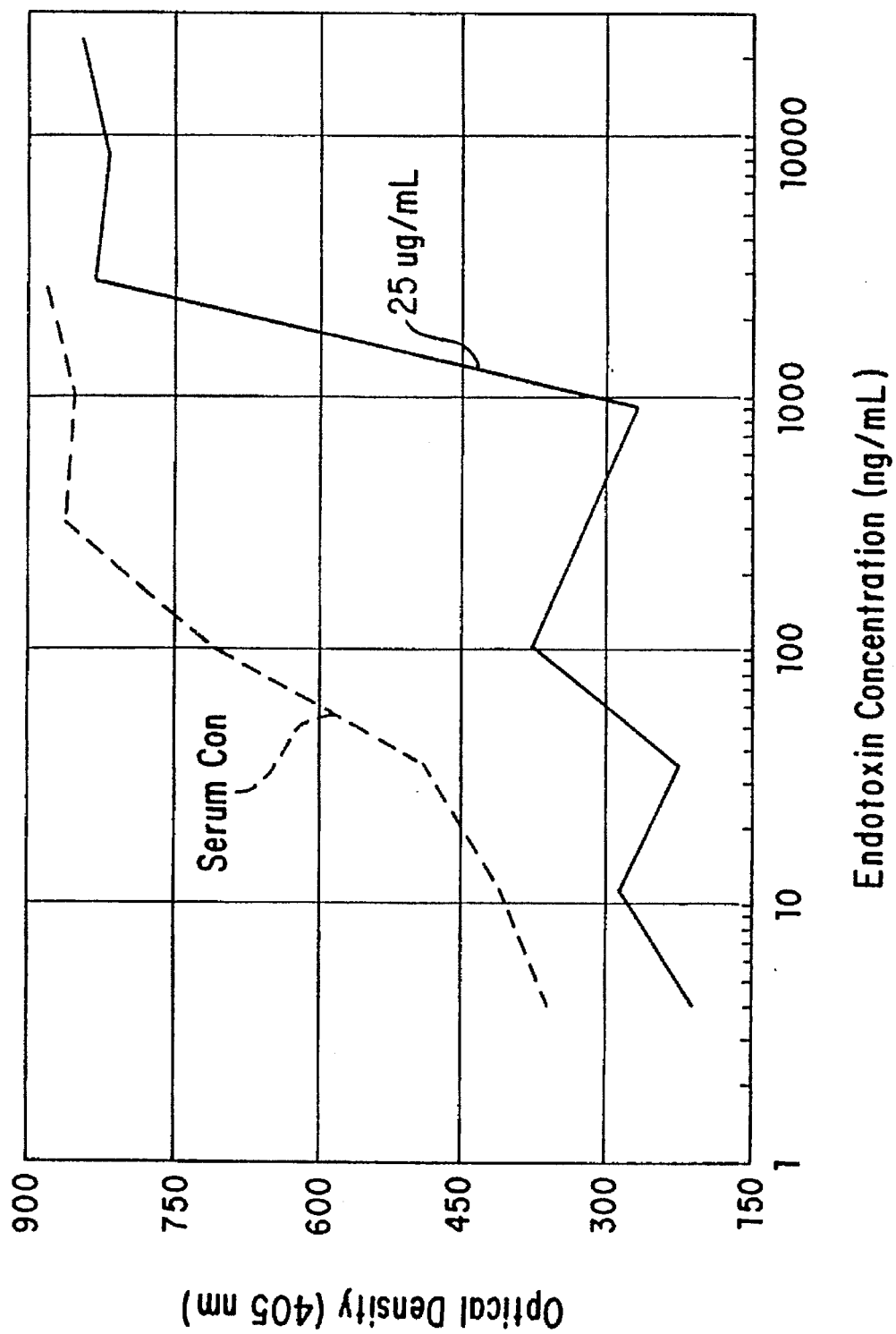
FIG. 14 demonstration of activity of Limulus endotoxin binding/neutralizing protein in the presence of total human serum. The dashed line represents serum alone as a control (68 nanograms of endotoxin per ml inactivated/neutralized). The solid line represents serum plus 25 micrograms/ml added endotoxin binding/neutralizing protein (1600 nanograms endotoxin per ml inactivated/neutralized).

The inventors examined a fluorescence maxima at 350 nm of the endotoxin binding protein at various concentrations of endotoxin. There was a proportional quenching of that fluorescence, indicative of a tight association. See FIG. 7. Other proteins as negative controls showed no such proportional change. See FIGS. 8 and 9. From this data, the inventors have been able to calculate the binding affinity constants between the present protein and endotoxin. See FIGS. 9–12.

The fluorescence quenching experiment may serve as the basis for an assay for endotoxin based on the physical change of a single protein upon exposure to endotoxin. The inventors have found that the quenching effect observed upon addition of endotoxin to the endotoxin binding protein does not appear to experience saturation up to a high concentration level of added endotoxin. In other words, although one would expect the relationship between concentration of endotoxin and quenching to be a nonlinear one, the linearity of the relationship extends over a remarkably wide range of concentration of endotoxin. This unexpected aspect of the present assay enables the assay to be used over a wider range of endotoxin concentrations than could have been expected. Ranges of the ratio of endotoxin binding protein to endotoxin that are expected to be effective are 0.1:1 to 5000:1, preferably 1:1 to 2000:1, most preferably 10:1 to 1000:1.

In a preferred embodiment of the present endotoxin assay using the present endotoxin binding protein, the response is amplified using a biosensor. Biosensors rely on a specific binding ligand immobilized on a solid (e.g., quartz) chip. Electrical potential between two electrodes, or the acoustic wave perturbation between two electrodes is measured.

The current method for measuring endotoxin is the Limulus amebocyte lysate assay. This involves a cascade of enzymes which are activated by endotoxin and result in the formation of a gel, analogous to a mammalian blood clot. Since multiple enzymes are involved, many substances interfere with the overall reaction, causing enhancement or inhibition. In addition, the key enzymes of the cascade are proteases so other proteolytic enzymes, such as trypsin, can cause gel formation. To eliminate these problems, samples containing interfering substances must be diluted beyond the point where they interfere. In many cases the dilution factor can be hundreds or thousands. The net effect is to decrease the sensitivity in measuring absolute endotoxin concentrations in those samples.

One of the promising potentials that a single endotoxin binding protein has is to eliminate the multiple interfering effects seen in the LAL assay. Even if the sensitivity were one tenth that of LAL, the lack of a need to dilute would compensate, making the sensitivity equivalent. Biosensors take advantage of specific binding affinities of such molecules. Antibodies are an example which have been used sound to the surface of a silicon chip they bind to their immunogen and cause a change in the surface which is measured electrically. Depending on the type of sensor, capacitance, resistance or acoustic wave changes are measurable. Depending on the concentrations and volumes of the samples, the time required for each measurement can be from seconds to minutes.

The electronic component of the biosensor could measure voltage (potentiometric), current (amperometric), light, sound, temperature or mass (piezoelectric). The biosensors of the present invention can be based on technology which is known, such as described in Biotechnology 5, 437–440 (1987), and Transducers 1987, the abstract entitled "Development of a Surface Acoustic Wave Biosensor", and "Recent Progress in Biosensor Development", Hall, E. A. H., Int. J. Biochem. 1988, 20(4), 357–62, each of which is incorporated herein by reference. Biosensor information is also contained in U.S. Pat. Nos. 4,721,677, 4,680,268, H 0,000,201, and 4,614,714, each of which is incorporated herein by reference.

An actual device employing a biosensor would be similar to a flow cell. The sample would enter, be exposed to the reactive surface and a measurement made. Depending on the chemistry of binding, the bound ligand could be washed off to regenerate the surface or left on to measure a cumulative response. This may be adapted to an in-line device to monitor endotoxin contaminating events.

Due to the compact nature of the electronics, a portable field unit is feasible. This could be used on-site for checking water purity or process cleanliness during pharmaceutical manufacture, kidney dialysis unit pyrogen checks, or any other application where the conventional LAL is used now. Since endotoxin is a component of gram negative bacterial cell walls, binding of whole bacteria should be measurable. An extension of this technology should make possible remote sensors to monitor water quality in the environment.

By coupling the binding protein to latex microspheres using a chemistry similar to that used to immobilize the protein on chromatographic resins or membranes, another method to quantitate endotoxin is constituted. By exposing latex microspheres coated with endotoxin binding protein (e.g., from Limulus) to endotoxin, the microspheres agglutinate. Such agglutination is commonly employed in assays based on antibodies to the specific ligand to be measured (Hechemy, K. E.; Michaelson, E. E. *Laboratory Menacement* 1984, 22(6):27.ff (Part I) and 22(7):26.f (Part II); Babson, A. L., Opper, C. A. and Crane L. J. American Journal of Clinical Pathology (1982), 77(4):424–9). In such techniques, the agglutination phenomenon is thought to be due to crosslinking between multiple binding sites on the antibody molecule complexing with multiple sites on the antigen. Due to the high ratio of endotoxin binding protein to endotoxin needed to be effective in our other solution experiments, it is thought the number of endotoxin binding sites on the protein is one or less. By covalently coupling many molecules of binding protein per microsphere, a multiple binding site reagent is created which is now possible to function as a specific agglutinin. Alternatively, the binding protein can be linked to one suspension of beads and endotoxin or lipid A linked to a second suspension. On mixing, these two suspensions will agglutinate. This may also be employed as an assay for endotoxin in solution by the ability of the free endotoxin to inhibit such agglutination. In this case, agglutination is inversely proportional to the unknown endotoxin concentration.

The invention now being generally described, it will now be illustrated in greater detail by the following examples, which are presented herein for illustration only and are not intended to be limiting of the present invention, unless so indicated.

EXAMPLES

Example 1

Assay in of in vitro Inactivated Endotoxin by Pyrogen Testing in Rabbits

*E. coli* endotoxin was prepared at 100 nanograms per ml. in Phosphate Buffered Saline (PBS). This was mixed with 200 micrograms of Limulus Endotoxin Binding Protein and incubated at 37 degrees Celsius for one hour. Control solutions were prepared of endotoxin (100 nanograms/ml) only and PBS only. Three vials of each of the three solutions were prepared containing 2 ml/vial. 1.5 ml of each solution was injected intravenously into individual 3 kilogram rabbits and their body temperatures measured continuously for six hours with data points recorded every 10 minutes. The final dose of endotoxin or inactivated endotoxin was 50 nanograms/kilogram.

In rabbits, a 5 nanograms/kilogram dose of endotoxin elicits a measurable fever response, showing a peak at one hour after injection. The present results showed the rabbits receiving only endotoxin at 50 nanograms/kilogram did indeed develop a body temperature elevated 1.64 (S.D. 0.236) degrees Celsius. Those rabbits receiving only PBS or endotoxin inactivated with Limulus Endotoxin Binding Protein maintained a normal body temperature.

Example 2

Assay of in vivo Prophylactic Efficacy of Limulus Endotoxin Binding Protein

Limulus Endotoxin Binding Protein is injected intravenously into rabbits at two dose levels, 5 micrograms/kilogram and 50 micrograms/kilogram. Control animals receive injections of PBS. Fifteen minutes later, all animals receive intravenous injections of 50 nanograms/kilogram *E. coli* endotoxin. Body temperature is monitored continuously over six hours and recorded every 10 minutes. The normal course of increase in temperature peaking at one hour after injection is seen in control animals preinjected with PBS only. Those animals receiving preinjection of endotoxin binding protein at 50 micrograms/kilogram showed an increase of 1.55 (S.D. 0.225) degrees Celsius. Animals receiving 5 micrograms/kilogram demonstrated temperature increases of 1.85 (S.D. 0.270).

Example 3

Assay of in vivo Therapeutic Efficacy of Limulus Endotoxin Binding Protein

*E. coli* endotoxin is injected intravenously into 9 rabbits at a dose of 50 nanograms/kg. After 15 minutes, three were injected intravenously with 5 micrograms Limulus Endotoxin Binding Protein, three were injected intravenously with 50 micrograms Limulus Endotoxin Binding Protein and three received PBS. Volumes of all injections were 0.5 ml/kg. Body temperatures are monitored for 6 hours and data collected every 10 minutes. Animals receiving endotoxin and the PBS only, manifest the normal peak fever response one hour after toxin administration. Those animals receiving therapeutic injections of the Limulus protein exhibit a much reduced fever response proportional to the amount of protein which is administered.

Example 4

Endotoxin Inactivating Potential of Limulus Endotoxin Binding Protein in Human Serum In order to assay the potential effectiveness of the endotoxin binding protein as a therapeutic or prophylactic agent for septic shock or related disorders in humans, the protein was tested for its ability to inactivate endotoxin in the presence of whole human serum. The assay was conducted in a 96-well tissue culture multiwell elates as described in detail in Novitsky et al., J. Clin. Micro., 20: 211–216 (1985). To each well were added in order 0.05 ml of serum only or serum with 25 micrograms/ml Limulus Endotoxin Binding Protein, 0.05 ml *E. coli* endotoxin solution. The plates were covered with Parafilm to prevent evaporation, agitated on a mechanical vibrating platform for 15 seconds and incubated at 37 degrees Celsius. Multiwell plates were then uncovered, and 0.1 ml of LAL was added to each well. The plates were subsequently handled and read as described for the LAL endotoxin assay. Serum with the added endotoxin binding protein was able to inactivate increasingly larger amounts of endotoxin (2,000 nanograms/ml) while serum alone was able to bind and/or inactivate only 80 nanograms/ml.

Example 5

Universality of Endotoxin Type Inactivated by the Limulus Endotoxin Binding Protein In order to investigate the mechanism of the endotoxin binding phenomenon and determine the breadth of endotoxin types against which the binding protein is effective, endotoxin from several species of Gram negative bacteria as well as lipid A were tested. These included endotoxin from *Klebsielia pneumonias, Serratia marcescens, Salmonella enteritidis, Escherichia coli* 0113 wild type, *E. coli* rough mutant (J-5), *Salmonella abortus equi*, and Lipid A from *S. minnesota* Re 595.

The endotoxin binding protein was mixed with the endotoxins or lipid A at a ratio of 5:1 to 1,000:1 in the presence of 10 millimolar Tris buffer, pH 6-8. In all cases the measurable endotoxin activity after mixing was reduced 85% to 99.5%.

Example 6

Summary

Limulus Endotoxin Binding Protein (EBP) protects rats from the lethal effects of lipopolysaccharide (LPS). The effects of premixed LPS and EBP (1:1 wt/wt) were compared to those of EBP or LPS alone. The material was administered to rats in groups. The endotoxin group exhibited 30% mortality; the group which received the combined EBP+LPS exhibited no deaths. In an in vitro experiment, vascular tissue was examined for contraction defects after preincubation with endotoxin, protein, or a mixture of endotoxin and protein. Endotoxin-incubated tissue exhibited reduced contraction to norepinephrine; coincubation with limulus protein protected against the supression.

Hematocytes from *Limulus polyphemus* contain a 12,000 dalton amphipathic protein with a high affinity for the lipid A portion of endotoxin. This protein is part of an anti-infection pathway of aggregation where rapid degranulation and clot formation are initiated when hematocytes are exposed to Gram-negative endotoxins. This endotoxin binding protein has been isolated and sequenced (SEQ. ID. NO. I). In vitro it binds to endotoxin with high affinity and neutralizes the lipopolysaccharide thus preventing it from being detected in the Limulus amebocyte assay. In a recent study which shows that this protein can protect endothelial cells in vitro from the toxic affect of endotoxin, the inventors examined the ability of the Limulus endotoxin binding-protein to protect rats from the toxic effects of endotoxin. Also, the ability of this protein to protect vascular tissue from the effects of endotoxin was examined in vitro experiments. The results of both in vivo and in-vitro experiments demonstrate that this protein exhibits a protective effect by neutralizing the endotoxin.

Methods

Protection From Endotoxemia

Male Sprague-Dawley rats (230–450 g) were given light Halothane anesthesia and then injected with the appropriate experimental treatment via the dorsal vein of the penis. Groups of rats received one of the following treatments;

1) LPS (*E. coli* 0111:B4, Sigma Chemical Company) in buffer, 0.15M NaCl buffered to pH 7.4 with 0.02M sodium phosphate, 2) A suspension of anti-LPS factor and LPS mixed 1:1 (wt/wt) in buffer, 3) Albumin mixed with LPS 1:1 (wt/wt), or 4) Only the Limulus protein incubated in buffer.

All solutions were incubated at 37° C. for one hour prior to injection. The volume injected (1.7 to 2.9 ml) depended on the weight of the rat and was adjusted to deliver an exact dose on a mg LPS/kg body weight basis. Animals were maintained on standard rat chow and water ad libitum. Survival was followed to 24 hours.

Aortic Ring Contraction

Rats were sacrificed by decapitation and the thoracic aorta excised and sectioned into rings for measures of contractile performance. Tissues from normal rats were incubated at 37° C. for 16 hours in DMEM (Dulbecco's Minimal Essential Medium) containing 5% fetal calf serum, 100 U penicillin, 100 ug streptomycin, and gassed with 95% $O_2$-5% $CO_2$. Experiments consisted of additions of either;

1) 10 ng/ml endotoxin, 2) 50 ng/ml endotoxin binding-protein, 3) a mixture of endotoxin and binding-protein (10 and 50 ng/ml), or 4) medium only during the 16 hr incubation period.

Contractile performance of rings suspended between two hooks in a 10 ml bath was assessed by measuring the tension as a function of cumulative doses of norepinephrine (NE) covering a range of 1 nM to 30 uM.

| Treatment | # Survivors/# Rats | % Survival | |
|---|---|---|---|
| Survival as a Function of Endotoxin/Neutralizing Protein (EBP) | | | |
| EXP[1] #1 | | | |
| LPS | 14/20 | 70 | |
| LPS + albumin | 9/20 | 40 | |
| LPS + EBP | 20/20 | 100[a,b] | Δ30 |
| EBP (only) | 13/15 | 87 | |
| EXP[2] #2 | | | |
| LPS | 9/28 | 32 | |
| LPS + albumin | 7/28 | 25 | |
| LPS + EBP | 14/27 | 50[c,d] | Δ18 |
| EBP (only) | 11/11 | 100 | |
| EBP (only) | 11/11 | 100 | |
| Survival as a Function of Native Endotoxin/Neutralizing Protein (nENP) and Recombinant Endotoxin Binding/Neutralizing Protein (rENP) | | | |
| LPS | 3/10 | 30 | |
| LPS + albumin | 5/10 | 50 | |
| LPS + r-EBP | 10/10 | 100[d,e] | Δ70 |
| EBP (only) | 10/10 | 100 | |

LPS = (15 mg/kg, #37F-4089) this lot # exhibits reduced toxicity
[a]p<.05 different from+LPS Buffer
[b]p<.05 different from LPS albumin
[2]LPS = (15 mg/kg, #39F-4030 and #37F-4019) all proteins = 15 mg/kg
[c,d]no significant different but trend consistent (p<.1)
LPS = (15 mg/kg, #39F-4030) all proteins = 15 mg/kg
[d]p<.05 different from LPS in buffer
[e]p<.05 different from LPS in albumin The invention now being fully described, it will be appreciated that the invention may be practiced otherwise than as specifically set forth herein.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 101 amino acids
( B ) TYPE: amino acid
( D ) TOPOLOGY: linear ( x i ) SEQUENCE DESCRIPTION: SEQ ID NO:1:

```
Asp Gly Ile Trp Thr Gln Leu Ile Phe Thr Leu Val Asn Asn Leu Ala
1               5                   10                  15

Thr Leu Trp Gln Ser Gly Asp Phe Gln Phe Leu Asp His Glu Cys His
            20                  25                  30

Tyr Arg Ile Lys Pro Thr Phe Arg Arg Leu Lys Trp Lys Tyr Lys Gly
        35                  40                  45

Lys Phe Trp Cys Pro Ser Trp Thr Ser Ile Thr Gly Arg Ala Thr Lys
    50                  55                  60

Ser Ser Arg Ser Gly Ala Val Glu His Ser Val Arg Asn Phe Val Gly
65                  70                  75                  80

Gln Ala Gly Ser Ser Gly Leu Ile Thr Gln Arg Gln Ala Glu Gln Phe
                85                  90                  95

Ile Ser Gln Tyr Asn
                100
```

( 2 ) INFORMATION FOR SEQ ID NO:2:

( i ) SEQUENCE CHARACTERISTICS:
( A ) LENGTH: 331 base pairs
( B ) TYPE: nucleic acid
( C ) STRANDEDNESS: both
( D ) TOPOLOGY: both ( x i ) SEQUENCE DESCRIPTION: SEQ ID NO:2:

```
GAG GCT GAA GCT GAC GGT ATC TGG ACC CAA TTG ATT TTC ACT TTG GTT        48
Glu Ala Glu Ala Asp Gly Ile Trp Thr Gln Leu Ile Phe Thr Leu Val
1               5                   10                  15

AAC ATT TTG GCC ACC TTA TGG CAG TCC GGT GAT TTT CAA TTC TTG GAC        96
Asn Ile Leu Ala Thr Leu Trp Gln Ser Gly Asp Phe Gln Phe Leu Asp
            20                  25                  30

CAC GAA TGT CAC TAC AGA ATC AAG CCA ACT TTC AGA AGA TTG AAG TGG       144
His Glu Cys His Tyr Arg Ile Lys Pro Thr Phe Arg Arg Leu Lys Trp
        35                  40                  45

AAA TAT AAG GGT AAA TTT TGG TGT CCA TCT TGG ACC TCT ATT ACT GGT       192
Lys Tyr Lys Gly Lys Phe Trp Cys Pro Ser Trp Thr Ser Ile Thr Gly
    50                  55                  60

AGA GCT ACC AAG TCT TCT AGA TCC GGT GCT GTC GAA CAC TCT GTT AGA       240
Arg Ala Thr Lys Ser Ser Arg Ser Gly Ala Val Glu His Ser Val Arg
65                  70                  75                  80

AAC TTC GTC GGT CCA GCT AAG TCT TCC GGT TTG ATC ACT GAA AGA CAA       288
Asn Phe Val Gly Pro Ala Lys Ser Ser Gly Leu Ile Thr Glu Arg Gln
                85                  90                  95

GCT GAA CAA TTC ATT TCT CAA TAC AAC TGATAAGCTT GAATTC                 331
Ala Glu Gln Phe Ile Ser Gln Tyr Asn
                100                 105
```

( 2 ) INFORMATION FOR SEQ ID NO:3:

(i) SEQUENCE CHARACTERISTICS:
    (A) LENGTH: 105 amino acids
    (B) TYPE: amino acid
    (C) TOPOLOGY: linear (xi) SEQUENCE DESCRIPTION: SEQ ID NO:3:

| | | | | | | | | | | | | | | | |
|---|---|---|---|---|---|---|---|---|---|---|---|---|---|---|---|
| Glu | Ala | Glu | Ala | Asp | Gly | Ile | Trp | Thr | Gln | Leu | Ile | Phe | Thr | Leu | Val |
| 1 | | | | 5 | | | | 10 | | | | | 15 | | |
| Asn | Ile | Leu | Ala | Thr | Leu | Trp | Gln | Ser | Gly | Asp | Phe | Gln | Phe | Leu | Asp |
| | | | 20 | | | | | 25 | | | | | 30 | | |
| His | Glu | Cys | His | Tyr | Arg | Ile | Lys | Pro | Thr | Phe | Arg | Arg | Leu | Lys | Trp |
| | | 35 | | | | | 40 | | | | | 45 | | | |
| Lys | Tyr | Lys | Gly | Lys | Phe | Trp | Cys | Pro | Ser | Trp | Thr | Ser | Ile | Thr | Gly |
| | 50 | | | | | 55 | | | | | 60 | | | | |
| Arg | Ala | Thr | Lys | Ser | Ser | Arg | Ser | Gly | Ala | Val | Glu | His | Ser | Val | Arg |
| 65 | | | | | 70 | | | | | 75 | | | | | 80 |
| Asn | Phe | Val | Gly | Pro | Ala | Lys | Ser | Ser | Gly | Leu | Ile | Thr | Glu | Arg | Gln |
| | | | | 85 | | | | | 90 | | | | | 95 | |
| Ala | Glu | Gln | Phe | Ile | Ser | Gln | Tyr | Asn | | | | | | | |
| | | | 100 | | | | | 105 | | | | | | | |

What is new and desired to be secured by Letters Patent of the United States is:

1. An endotoxin binding protein having SEQ. ID NO. III immobilized on a solid phase support.

2. The immobilized endotoxin protein of claim 1, wherein said solid phase support is a chromatographic resin or a membrane.

3. The immobilized endotoxin binding protein of claim 1, wherein said solid phase support is latex microspheres.

* * * * *

UNITED STATES PATENT AND TRADEMARK OFFICE
CERTIFICATE OF CORRECTION

PATENT NO. : 5,627,266

DATED : May 6, 1997

INVENTORS : Wainwright *et al.*

It is certified that an error appears in the above-identified patent and that said Letters Patent is hereby corrected as shown below.

In Column 15, at lines 52-53, please delete "the inventors examined"; and at line 54, after "endotoxin" please insert --was examined--.

Signed and Sealed this

Twenty-eighth Day of October, 1997

*Attest:*

BRUCE LEHMAN

*Attesting Officer*     *Commissioner of Patents and Trademarks*